(12) United States Patent
Boettcher et al.

(10) Patent No.: US 9,023,791 B2
(45) Date of Patent: May 5, 2015

(54) FIBROBLAST GROWTH FACTOR 21 MUTATIONS

(75) Inventors: Brian R. Boettcher, Winchester, MA (US); Shari L. Caplan, Lunenburg, MA (US); Douglas S. Daniels, Arlington, MA (US); Bernhard H. Geierstanger, Solana Beach, CA (US); Norio Hamamatsu, Belmont, MA (US); Stuart Licht, Cambridge, MA (US); Andreas Loew, Somerville, MA (US); Stephen Craig Weldon, Leominster, MA (US)

(73) Assignees: Novartis AG, Basel (CH); IRM LLC, Hamilton (BM)

( * ) Notice: Subject to any disclaimer, the term of this patent is extended or adjusted under 35 U.S.C. 154(b) by 0 days.

(21) Appl. No.: 13/296,343

(22) Filed: Nov. 15, 2011

(65) Prior Publication Data

US 2012/0129766 A1    May 24, 2012

Related U.S. Application Data

(60) Provisional application No. 61/415,476, filed on Nov. 19, 2010.

(51) Int. Cl.
*A61K 38/18* (2006.01)
*C07K 14/50* (2006.01)

(52) U.S. Cl.
CPC ............. *C07K 14/50* (2013.01); *C07K 2319/00* (2013.01); *C07K 2319/30* (2013.01)

(58) Field of Classification Search
CPC .......................... A61K 38/1825; C07K 14/50
See application file for complete search history.

(56) References Cited

U.S. PATENT DOCUMENTS

| | | | |
|---|---|---|---|
| 2009/0118190 A1* | 5/2009 | Beals et al. | 514/12 |
| 2010/0216715 A1* | 8/2010 | Tagmose et al. | 514/12 |
| 2011/0195895 A1* | 8/2011 | Walker et al. | 514/4.8 |
| 2012/0052069 A1* | 3/2012 | Belouski et al. | 424/134.1 |

FOREIGN PATENT DOCUMENTS

| | | |
|---|---|---|
| WO | 2005061712 A1 | 7/2005 |
| WO | 2008121563 A2 | 10/2008 |
| WO | 2010065439 A1 | 6/2010 |

OTHER PUBLICATIONS

"Human Fibroblast Growth Factor 21 Mutein Q156E . . . " Sep. 8, 2005 Database Accession No. AEB19076.
Micanovic et al., "Different roles of N- and C-Termini in the Functional Activity of FGF21" Journal of Cellular Physiology 219(2):227-234 (May 1, 2009).
Yie et al., "FGF21 N- and C-termini play different roles in receptor interaction and activation," FEBS Letters 583 (1):19-24 (Jan. 5, 2009).

* cited by examiner

*Primary Examiner* — Christine J Saoud
(74) *Attorney, Agent, or Firm* — Paul J. Paglierani

(57) ABSTRACT

The present invention provides novel polypeptide and protein variants of fibroblast growth factor 21 (FGF21) and pharmaceutical compositions comprising FGF21 polypeptide and protein variants.

39 Claims, 3 Drawing Sheets

SEQUENCE LISTING

```
<160> NUMBER OF SEQ ID NOS: 49

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190
```

```
Pro Leu Ser Met Val Gly Pro Ser Gln Gly Arg Ser Pro Ser Tyr Ala
        195                 200                 205
Ser
```

<210> SEQ ID NO 2
<211> LENGTH: 630
<212> TYPE: DNA
<213> ORGANISM: Homo sapiens

<400> SEQUENCE: 2

```
atggactcgg acgagaccgg gttcgagcac tcaggactgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac    180
ctggagatca ggaggatgg gacggtgggg ggcgctgctg accagagccc cgaaagtctc     240
ctgcagctga aagccttgaa gccgggagtt attcaaatct tgggagtcaa gacatccagg    300
ttcctgtgcc agcggccaga tggggccctg tatggatcgc tccactttga ccctgaggcc    360
tgcagcttcc gggagctgct tcttgaggac ggatacaatg tttaccagtc gaagcccac     420
ggcctcccgc tgcacctgcc agggaacaag tccccacacc gggaccctgc acccgagga     480
ccagctcgct tcctgccact accaggcctg ccccccgcac tcccggagcc acccggaatc    540
ctggcccccc agccccccga tgtgggctcc tcggaccctc tgagcatggt gggaccttcc    600
cagggccgaa gccccagcta cgcttcctga                                      630
```

<210> SEQ ID NO 3
<211> LENGTH: 181
<212> TYPE: PRT
<213> ORGANISM: Homo sapiens

<400> SEQUENCE: 3

```
His Pro Ile Pro Asp Ser Ser Pro Leu Leu Gln Phe Gly Gly Gln Val
  1               5                  10                  15
Arg Gln Arg Tyr Leu Tyr Thr Asp Asp Ala Gln Gln Thr Glu Ala His
             20                  25                  30
Leu Glu Ile Arg Glu Asp Gly Thr Val Gly Gly Ala Ala Asp Gln Ser
         35                  40                  45
Pro Glu Ser Leu Leu Gln Leu Lys Ala Leu Lys Pro Gly Val Ile Gln
     50                  55                  60
Ile Leu Gly Val Lys Thr Ser Arg Phe Leu Cys Gln Arg Pro Asp Gly
 65                  70                  75                  80
Ala Leu Tyr Gly Ser Leu His Phe Asp Pro Glu Ala Cys Ser Phe Arg
                 85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
            180
```

-continued

<210> SEQ ID NO 4
<211> LENGTH: 15
<212> TYPE: DNA
<213> ORGANISM: Artificial Sequence
<220> FEATURE:
<223> OTHER INFORMATION: Linker

<400> SEQUENCE: 4
ggggsggggs ggggs        15

<210> SEQ ID NO 5
<211> LENGTH: 177
<212> TYPE: PRT
<213> ORGANISM: Homo sapiens

<400> SEQUENCE: 5

Asp Ser Ser Pro Leu Leu Gln Phe Gly Gly Gln Val Arg Gln Arg Tyr
 1               5                  10                  15

Leu Tyr Thr Asp Asp Ala Gln Glu Thr Glu Ala His Leu Glu Ile Arg
            20                  25                  30

Glu Asp Gly Thr Ala Gly Gly Ala Ala Asp Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Gly Pro Asp Gly Ala Leu Tyr Gly
65                  70                  75                  80

Ser Leu His Phe Asp Pro Glu Ala Cys Ser Phe Arg Glu Leu Val Leu
                85                  90                  95

Glu Asp Gly Tyr Asn Val Tyr Gln Ser Glu Ala His Gly Leu Pro Leu
            100                 105                 110

His Leu Pro Gly His Lys Ser Pro His Arg Asp Pro Ala Pro Arg Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Glu Pro Pro Asp Val Gly Ser Ser Asp
145                 150                 155                 160

Pro Leu Ser Met Val Gly Pro Ser Gln Gly Arg Ser Pro Ser Tyr Thr
                165                 170                 175

Ser

<210> SEQ ID NO 6
<211> LENGTH: 177
<212> TYPE: PRT
<213> ORGANISM: Homo sapiens

<400> SEQUENCE: 6

Asp Ser Ser Pro Leu Leu Gln Phe Gly Gly Gln Val Arg Gln Arg Tyr
 1               5                  10                  15

Leu Tyr Thr Asp Asp Ala Gln Asn Thr Glu Ala His Leu Glu Ile Arg
            20                  25                  30

Glu Asp Gly Thr Ala Gly Gly Ala Ala Asp Gln Ser Pro Glu Ser Leu
        35                  40                  45

Leu Asn Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Val Leu

```
                85                  90                  95
Glu Asp Gly Tyr Asn Val Tyr Gln Ser Glu Ala His Gly Leu Pro Leu
            100                 105                 110

His Leu Pro Gly Gln Lys Ser Pro His Arg Asp Pro Ala Pro Arg Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Asn Pro Pro Asp Val Gly Ser Ser Asp
145                 150                 155                 160

Pro Leu Ser Met Val Gly Pro Ser Gln Gly Arg Ser Pro Ser Tyr Thr
                165                 170                 175

Ser

<210> SEQ ID NO 7
<211> LENGTH: 177
<212> TYPE: PRT
<213> ORGANISM: Homo sapiens

<400> SEQUENCE: 7

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 8
<211> LENGTH: 177
<212> TYPE: PRT
<213> ORGANISM: Homo sapiens

<400> SEQUENCE: 8

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45
```

Leu Gln Leu Lys Ala Leu Lys Pro Gly Val Ile Gln Ile Leu Gly Val
 50                  55                  60

Gln Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Gly Asn Lys Ser Pro His Arg Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 9
<211> LENGTH: 177
<212> TYPE: PRT
<213> ORGANISM: Homo sapiens

<400> SEQUENCE: 9

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 10
<211> LENGTH: 177
<212> TYPE: PRT
<213> ORGANISM: Homo sapiens

<400> SEQUENCE: 10

Asp Ser Ser Pro Leu Leu Gln Phe Gly Gly Gln Val Arg Gln Arg Tyr
1               5                   10                  15

```
Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Gln Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Gly Asn Lys Ser Pro His Arg Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 11
<211> LENGTH: 177
<212> TYPE: PRT
<213> ORGANISM: Homo sapiens

<400> SEQUENCE: 11

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Gly Asn Lys Ser Pro His Arg Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 12
<211> LENGTH: 177
```

```
<212> TYPE: PRT
<213> ORGANISM: Homo sapiens

<400> SEQUENCE: 12

Asp Ser Ser Pro Leu Leu Gln Phe Gly Gly Gln Val Arg Gln Arg Tyr
1               5                   10                  15

Leu Tyr Thr Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
            35                  40                  45

Leu Gln Leu Lys Ala Leu Lys Pro Gly Val Ile Gln Ile Leu Gly Val
        50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Gly Asn Lys Ser Pro His Arg Asp Pro Ala Ser Gln Gly
            115                 120                 125

Pro Ala Arg Phe Leu Pro Leu Pro Gly Leu Pro Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 13
<211> LENGTH: 177
<212> TYPE: PRT
<213> ORGANISM: Homo sapiens

<400> SEQUENCE: 13

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
            35                  40                  45

Leu Glu Leu Lys Ala Leu Lys Pro Gly Val Ile Gln Ile Leu Gly Val
        50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
            115                 120                 125

Pro Ala Arg Phe Leu Pro Leu Pro Gly Leu Pro Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
```

```
                    165                 170                 175

Ser

<210> SEQ ID NO 14
<211> LENGTH: 177
<212> TYPE: PRT
<213> ORGANISM: Homo sapiens

<400> SEQUENCE: 14

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Gln Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 15
<211> LENGTH: 177
<212> TYPE: PRT
<213> ORGANISM: Homo sapiens

<400> SEQUENCE: 15

Asp Ser Ser Pro Leu Leu Gln Phe Gly Gly Gln Val Arg Gln Arg Tyr
1               5                   10                  15

Leu Tyr Thr Asp Asp Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
        115                 120                 125
```

```
Pro Ala Arg Phe Leu Pro Leu Pro Gly Leu Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 16
<211> LENGTH: 177
<212> TYPE: PRT
<213> ORGANISM: Homo sapiens

<400> SEQUENCE: 16

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
        115                 120                 125

Pro Ala Arg Phe Leu Pro Leu Pro Gly Leu Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 17
<211> LENGTH: 177
<212> TYPE: PRT
<213> ORGANISM: Homo sapiens

<400> SEQUENCE: 17

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95
```

Glu Asn Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
            115                 120                 125

Pro Ala Arg Phe Leu Pro Leu Pro Gly Leu Pro Pro Ala Pro Pro Glu
130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 18
<211> LENGTH: 177
<212> TYPE: PRT
<213> ORGANISM: Homo sapiens

<400> SEQUENCE: 18

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Gln Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
            115                 120                 125

Pro Ala Arg Phe Leu Pro Leu Pro Gly Leu Pro Pro Ala Leu Pro Glu
130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 19
<211> LENGTH: 177
<212> TYPE: PRT
<213> ORGANISM: Homo sapiens

<400> SEQUENCE: 19

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val

```
                    50                  55                  60

Lys Ala Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                     85                  90                  95

Glu Asn Gly Tyr Asn Val Tyr Gln Ser Glu Ala His Gly Leu Pro Leu
                    100                 105                 110

His Leu Pro Gly Asn Arg Ser Pro His Arg Asp Pro Ala Pro Gln Gly
                    115                 120                 125

Pro Ala Arg Phe Leu Pro Leu Pro Gly Leu Pro Pro Ala Leu Pro Glu
                130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                    165                 170                 175

Ser

<210> SEQ ID NO 20
<211> LENGTH: 177
<212> TYPE: PRT
<213> ORGANISM: Homo sapiens

<400> SEQUENCE: 20

Asp Ser Ser Pro Leu Leu Gln Phe Gly Gly Gln Val Arg Gln Arg Tyr
 1               5                  10                  15

Leu Tyr Thr Asp Asp Ala Gln Gln Thr Glu Ser His Leu Glu Ile Arg
                 20                  25                  30

Glu Asp Gly Thr Val Gly Gly Ala Ala His Gln Ser Pro Glu Ser Leu
             35                  40                  45

Leu Glu Leu Lys Ala Leu Lys Pro Gly Val Ile Gln Ile Leu Gly Val
 50                  55                  60

Lys Thr Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                     85                  90                  95

Glu Asn Gly Tyr Asn Val Tyr Gln Ser Glu Ala His Gly Leu Pro Leu
                    100                 105                 110

His Leu Pro Gly Asn Arg Ser Pro His Arg Asp Pro Ala Pro Gln Gly
                    115                 120                 125

Pro Ala Arg Phe Leu Pro Leu Pro Gly Leu Pro Pro Ala Leu Pro Glu
                130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                    165                 170                 175

Ser

<210> SEQ ID NO 21
<211> LENGTH: 177
<212> TYPE: PRT
<213> ORGANISM: Homo sapiens

<400> SEQUENCE: 21

Asp Ser Ser Pro Leu Leu Gln Phe Gly Gly Gln Val Arg Gln Arg Tyr
 1               5                  10                  15
```

```
Leu Tyr Thr Asp Asp Ala Gln Gln Thr Glu Ser His Leu Glu Ile Arg
             20                  25                  30

Glu Asp Gly Thr Val Gly Gly Ala Ala His Gln Ser Pro Glu Ser Leu
         35                  40                  45

Leu Gln Leu Lys Ala Leu Lys Pro Gly Val Ile Gln Ile Leu Gly Val
     50                  55                  60

Gln Thr Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
        115                 120                 125

Pro Ala Arg Phe Leu Pro Leu Pro Gly Leu Pro Pro Ala Leu Pro Glu
130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser
```

<210> SEQ ID NO 22
<211> LENGTH: 177
<212> TYPE: PRT
<213> ORGANISM: Homo sapiens

<400> SEQUENCE: 22

```
Asp Ser Ser Pro Leu Leu Gln Phe Gly Gly Gln Val Arg Gln Arg Tyr
 1               5                  10                  15

Leu Tyr Thr Asp Asp Ala Gln Gln Thr Glu Ser His Leu Glu Ile Arg
             20                  25                  30

Glu Asp Gly Thr Val Gly Gly Ala Ala His Gln Ser Pro Glu Ser Leu
         35                  40                  45

Leu Gln Leu Lys Ala Leu Lys Pro Gly Val Ile Gln Ile Leu Gly Val
     50                  55                  60

Lys Ala Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Pro Gln Gly
        115                 120                 125

Pro Ala Arg Phe Leu Pro Leu Pro Gly Leu Pro Pro Ala Leu Pro Glu
130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser
```

<210> SEQ ID NO 23
<211> LENGTH: 177
<212> TYPE: PRT

<213> ORGANISM: Homo sapiens

<400> SEQUENCE: 23

```
Asp Ser Ser Pro Leu Leu Gln Phe Gly Gly Gln Val Arg Gln Arg Tyr
1               5                   10                  15
Leu Tyr Thr Asp Asp Gln Gln Thr Glu Ala His Leu Glu Ile Arg
            20                  25                  30
Glu Asp Gly Thr Val Gly Gly Ala Ala His Gln Ser Pro Glu Ser Leu
        35                  40                  45
Leu Gln Leu Lys Ala Leu Lys Pro Gly Val Ile Gln Ile Leu Gly Val
    50                  55                  60
Gln Thr Ser Arg Phe Leu Cys Gln Lys Pro Asp Gly Ala Leu Tyr Gly
65                  70                  75                  80
Ser Leu His Phe Asp Pro Glu Ala Cys Ser Phe Arg Glu Leu Leu Leu
                85                  90                  95
Glu Asn Gly Tyr Asn Val Tyr Gln Ser Glu Ala His Gly Leu Pro Leu
            100                 105                 110
His Leu Pro Gly Asn Arg Ser Pro His Arg Asp Pro Ala Ser Gln Gly
        115                 120                 125
Pro Ala Arg Phe Leu Pro Leu Pro Gly Leu Pro Pro Ala Leu Pro Glu
    130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Ala Arg Ser Pro Ser Tyr Ala
                165                 170                 175
Ser
```

<210> SEQ ID NO 24
<211> LENGTH: 177
<212> TYPE: PRT
<213> ORGANISM: Homo sapiens

<400> SEQUENCE: 24

```
Asp Ser Ser Pro Leu Leu Gln Phe Gly Gly Gln Val Arg Gln Arg Tyr
1               5                   10                  15
Leu Tyr Thr Asp Asp Ala Gln Glu Thr Glu Ala His Leu Glu Ile Arg
            20                  25                  30
Glu Asp Gly Thr Val Gly Gly Ala Ala His Gln Ser Pro Glu Ser Leu
        35                  40                  45
Leu Gln Leu Lys Ala Leu Lys Pro Gly Val Ile Gln Ile Leu Gly Val
    50                  55                  60
Gln Thr Ser Arg Phe Leu Cys Gln Lys Pro Asp Gly Ala Leu Tyr Gly
65                  70                  75                  80
Ser Leu His Phe Asp Pro Glu Ala Cys Ser Phe Arg Glu Leu Leu Leu
                85                  90                  95
Glu Asn Gly Tyr Asn Val Tyr Gln Ser Glu Ala His Gly Leu Pro Leu
            100                 105                 110
His Leu Pro Gly Asn Arg Ser Pro His Arg Asp Pro Ala Ser Gln Gly
        115                 120                 125
Pro Ala Arg Phe Leu Pro Leu Pro Gly Leu Pro Pro Ala Leu Pro Glu
    130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Ala Arg Ser Pro Ser Tyr Ala
                165                 170                 175
```

Ser

```
<210> SEQ ID NO 25
<211> LENGTH: 177
<212> TYPE: PRT
<213> ORGANISM: Homo sapiens

<400> SEQUENCE: 25
```

| Asp | Ser | Ser | Pro | Leu | Val | Gln | Phe | Gly | Gly | Gln | Val | Arg | Gln | Arg | Tyr |
|---|---|---|---|---|---|---|---|---|---|---|---|---|---|---|---|
| 1 | | | | 5 | | | | | 10 | | | | | 15 | |
| Leu | Tyr | Thr | Asp | Asp | Ala | Gln | Gln | Thr | Glu | Ala | His | Leu | Glu | Ile | Arg |
| | | | 20 | | | | | 25 | | | | | 30 | | |
| Glu | Asp | Gly | Thr | Val | Gly | Gly | Ala | Ala | His | Gln | Ser | Pro | Glu | Ser | Leu |
| | | | 35 | | | | | 40 | | | | | 45 | | |
| Leu | Gln | Leu | Lys | Ala | Leu | Lys | Pro | Gly | Val | Ile | Gln | Ile | Leu | Gly | Val |
| | 50 | | | | | 55 | | | | | 60 | | | | |
| Lys | Thr | Ser | Arg | Phe | Leu | Cys | Gln | Lys | Pro | Asp | Gly | Ala | Leu | Tyr | Gly |
| 65 | | | | | 70 | | | | | 75 | | | | | 80 |
| Ser | Leu | His | Phe | Asp | Pro | Glu | Ala | Cys | Ser | Phe | Arg | Glu | Leu | Leu | Leu |
| | | | | 85 | | | | | 90 | | | | | 95 | |
| Glu | Asn | Gly | Tyr | Asn | Val | Tyr | Gln | Ser | Glu | Ala | His | Ser | Leu | Pro | Leu |
| | | | 100 | | | | | 105 | | | | | 110 | | |
| His | Leu | Pro | Gly | Asn | Lys | Ser | Pro | His | Arg | Asp | Pro | Ala | Ser | Gln | Gly |
| | | | 115 | | | | | 120 | | | | | 125 | | |
| Pro | Ala | Arg | Phe | Leu | Pro | Leu | Pro | Gly | Leu | Pro | Pro | Ala | Leu | Pro | Glu |
| | | | 130 | | | | | 135 | | | | | 140 | | |
| Pro | Pro | Gly | Ile | Leu | Ala | Pro | Gln | Pro | Pro | Asp | Val | Gly | Ser | Ser | Asp |
| 145 | | | | | 150 | | | | | 155 | | | | | 160 |
| Pro | Leu | Ser | Met | Val | Gly | Pro | Ser | Gln | Ala | Arg | Ser | Pro | Ser | Tyr | Ala |
| | | | | 165 | | | | | 170 | | | | | 175 | |

Ser

```
<210> SEQ ID NO 26
<211> LENGTH: 177
<212> TYPE: PRT
<213> ORGANISM: Homo sapiens

<400> SEQUENCE: 26
```

| Asp | Ser | Ser | Pro | Leu | Leu | Gln | Phe | Gly | Gly | Gln | Val | Arg | Gln | Arg | Tyr |
|---|---|---|---|---|---|---|---|---|---|---|---|---|---|---|---|
| 1 | | | | 5 | | | | | 10 | | | | | 15 | |
| Leu | Tyr | Thr | Asp | Asp | Ala | Gln | Glu | Thr | Glu | Ala | His | Leu | Glu | Ile | Arg |
| | | | 20 | | | | | 25 | | | | | 30 | | |
| Glu | Asp | Gly | Thr | Val | Gly | Gly | Ala | Ala | His | Gln | Ser | Pro | Glu | Ser | Leu |
| | | | 35 | | | | | 40 | | | | | 45 | | |
| Leu | Glu | Leu | Lys | Ala | Leu | Lys | Pro | Gly | Val | Ile | Gln | Ile | Leu | Gly | Val |
| | 50 | | | | | 55 | | | | | 60 | | | | |
| Lys | Thr | Ser | Arg | Phe | Leu | Cys | Gln | Lys | Pro | Asp | Gly | Ala | Leu | Tyr | Gly |
| 65 | | | | | 70 | | | | | 75 | | | | | 80 |
| Ser | Leu | His | Phe | Asp | Pro | Glu | Ala | Cys | Ser | Phe | Arg | Glu | Leu | Leu | Leu |
| | | | | 85 | | | | | 90 | | | | | 95 | |
| Glu | Asn | Gly | Tyr | Asn | Val | Tyr | Gln | Ser | Glu | Ala | His | Gly | Leu | Pro | Leu |
| | | | 100 | | | | | 105 | | | | | 110 | | |
| His | Leu | Pro | Gly | Asn | Arg | Ser | Pro | His | Arg | Asp | Pro | Ala | Ser | Gln | Gly |
| | | | 115 | | | | | 120 | | | | | 125 | | |
| Pro | Ala | Arg | Phe | Leu | Pro | Leu | Pro | Gly | Leu | Pro | Pro | Ala | Pro | Pro | Glu |

```
            130                 135                 140
Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 27
<211> LENGTH: 177
<212> TYPE: PRT
<213> ORGANISM: Homo sapiens

<400> SEQUENCE: 27

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
                20                  25                  30

Glu Asp Gly Thr Val Gly Gly Ala Ala His Gln Ser Pro Glu Ser Leu
            35                  40                  45

Leu Glu Leu Lys Ala Leu Lys Pro Gly Val Ile Gln Ile Leu Gly Val
50                  55                  60

Lys Thr Ser Arg Phe Leu Cys Gln Lys Pro Asp Gly Thr Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Ser Gln Gly
        115                 120                 125

Pro Ala Arg Phe Leu Pro Leu Pro Gly Leu Pro Pro Ala Pro Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 28
<211> LENGTH: 177
<212> TYPE: PRT
<213> ORGANISM: Homo sapiens

<400> SEQUENCE: 28

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
                20                  25                  30

Glu Asp Gly Thr Ala Gly Gly Ala Ala His Gln Ser Pro Glu Ser Leu
            35                  40                  45

Leu Glu Leu Lys Ala Leu Lys Pro Gly Val Ile Gln Ile Leu Gly Val
50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95
```

```
Glu Asn Gly Tyr Asn Val Tyr Gln Ser Glu Ala His Gly Leu Pro Leu
            100                 105                 110

His Leu Pro Gly Asn Arg Ser Pro His Arg Asp Pro Ala Ser Gln Gly
        115                 120                 125

Pro Ala Arg Phe Leu Pro Leu Pro Gly Leu Pro Pro Ala Pro Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser
```

<210> SEQ ID NO 29
<211> LENGTH: 177
<212> TYPE: PRT
<213> ORGANISM: Homo sapiens

<400> SEQUENCE: 29

```
Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Ala Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Gly Asn Lys Ser Pro His Arg Asp Pro Ala Ser Gln Gly
        115                 120                 125

Pro Ala Arg Phe Leu Pro Leu Pro Gly Leu Pro Pro Ala Pro Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser
```

<210> SEQ ID NO 30
<211> LENGTH: 177
<212> TYPE: PRT
<213> ORGANISM: Homo sapiens

<400> SEQUENCE: 30

```
Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60
```

```
Lys Ala Ser Arg Phe Leu Cys Gln Arg Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Thr His Gly Leu Pro Leu
                100                 105                 110

His Leu Pro Gly Asn Arg Ser Pro His Arg Asp Pro Ala Ser Gln Gly
            115                 120                 125

Pro Ala Arg Phe Leu Pro Leu Pro Gly Leu Pro Pro Ala Pro Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser
```

<210> SEQ ID NO 31
<211> LENGTH: 177
<212> TYPE: PRT
<213> ORGANISM: Homo sapiens

<400> SEQUENCE: 31

```
Asp Ser Ser Pro Leu Leu Gln Phe Gly Gly Gln Val Arg Gln Arg Tyr
 1               5                  10                  15

Leu Tyr Thr Asp Asp Ala Gln Gln Thr Glu Ala His Leu Glu Ile Arg
                 20                  25                  30

Glu Asp Gly Thr Val Gly Gly Ala Ala His Gln Ser Pro Glu Ser Leu
             35                  40                  45

Leu Gln Leu Lys Ala Leu Lys Pro Gly Val Ile Gln Ile Leu Gly Val
         50                  55                  60

Lys Thr Ser Arg Phe Leu Cys Gln Arg Pro Asp Gly Thr Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Thr His Gly Leu Pro Leu
                100                 105                 110

His Leu Pro Gly Asn Arg Ser Pro His Arg Asp Pro Ala Ser Gln Gly
            115                 120                 125

Pro Ala Arg Phe Leu Pro Leu Pro Gly Leu Pro Pro Ala Pro Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser
```

<210> SEQ ID NO 32
<211> LENGTH: 177
<212> TYPE: PRT
<213> ORGANISM: Homo sapiens

<400> SEQUENCE: 32

```
Asp Ser Ser Pro Leu Leu Gln Phe Gly Gly Gln Val Arg Gln Arg Tyr
 1               5                  10                  15

Leu Tyr Thr Asp Asp Ala Cys Gln Thr Glu Ala His Leu Glu Ile Arg
```

```
                  20                  25                  30
Glu Asp Gly Thr Val Gly Gly Ala Ala His Gln Ser Pro Glu Ser Leu
             35                  40                  45

Leu Glu Leu Lys Ala Leu Lys Pro Gly Val Ile Gln Ile Leu Gly Val
 50                  55                  60

Lys Thr Ser Arg Phe Leu Cys Gln Arg Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Ala His Gly Leu Pro Leu
                100                 105                 110

His Leu Pro Cys Asn Arg Ser Pro His Arg Asp Pro Ala Ser Gln Gly
                115                 120                 125

Pro Ala Arg Phe Leu Pro Leu Pro Gly Leu Pro Pro Ala Pro Pro Glu
            130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                    165                 170                 175

Ser

<210> SEQ ID NO 33
<211> LENGTH: 177
<212> TYPE: PRT
<213> ORGANISM: Homo sapiens

<400> SEQUENCE: 33

Asp Ser Ser Pro Leu Leu Gln Phe Gly Gly Gln Val Arg Gln Arg Tyr
 1               5                  10                  15

Leu Tyr Thr Asp Asp Ala Cys Gln Thr Glu Ala His Leu Glu Ile Arg
                 20                  25                  30

Glu Asp Gly Thr Val Gly Gly Ala Ala His Gln Ser Pro Glu Ser Leu
             35                  40                  45

Leu Glu Leu Lys Ala Leu Lys Pro Gly Val Ile Gln Ile Leu Gly Val
 50                  55                  60

Lys Thr Ser Arg Phe Leu Cys Gln Arg Pro Asp Gly Thr Leu Tyr Gly
 65                  70                  75                  80

Ser Leu His Phe Asp Pro Glu Ala Cys Ser Phe Arg Glu Leu Leu Leu
                 85                  90                  95

Glu Asn Gly Tyr Asn Val Tyr Gln Ser Glu Ala His Gly Leu Pro Leu
                100                 105                 110

His Leu Pro Cys Asn Arg Ser Pro His Arg Asp Pro Ala Ser Arg Gly
                115                 120                 125

Pro Ala Arg Phe Leu Pro Leu Pro Gly Leu Pro Pro Ala Pro Pro Glu
            130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                    165                 170                 175

Ser

<210> SEQ ID NO 34
<211> LENGTH: 177
<212> TYPE: PRT
<213> ORGANISM: Homo sapiens
```

<400> SEQUENCE: 34

```
Asp Ser Ser Pro Leu Leu Gln Phe Gly Gly Gln Val Arg Gln Arg Tyr
1               5                   10                  15
Leu Tyr Thr Asp Asp Ala Cys Gln Thr Glu Ala His Leu Glu Ile Arg
            20                  25                  30
Glu Asp Gly Thr Ala Gly Gly Ala Ala His Gln Ser Pro Glu Ser Leu
        35                  40                  45
Leu Glu Leu Lys Ala Leu Lys Pro Gly Val Ile Gln Ile Leu Gly Val
    50                  55                  60
Lys Thr Ser Arg Phe Leu Cys Gln Arg Pro Asp Gly Ala Leu Tyr Gly
65                  70                  75                  80
Ser Leu His Phe Asp Pro Glu Ala Cys Ser Phe Arg Glu Leu Leu Leu
                85                  90                  95
Glu Asn Gly Tyr Asn Val Tyr Gln Ser Glu Ala His Gly Leu Pro Leu
            100                 105                 110
His Leu Pro Cys Asn Arg Ser Pro His Arg Asp Pro Ala Ser Arg Gly
        115                 120                 125
Pro Ala Arg Phe Leu Pro Leu Pro Gly Leu Pro Pro Ala Pro Pro Glu
    130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Gly Arg Ser Pro Ser Tyr Ala
                165                 170                 175
Ser
```

<210> SEQ ID NO 35
<211> LENGTH: 177
<212> TYPE: PRT
<213> ORGANISM: Homo sapiens

<400> SEQUENCE: 35

```
Asp Ser Ser Pro Leu Leu Gln Phe Gly Gly Gln Val Arg Gln Arg Tyr
1               5                   10                  15
Leu Tyr Thr Asp Asp Ala Cys Gln Thr Glu Ala His Leu Glu Ile Arg
            20                  25                  30
Glu Asp Gly Thr Val Gly Gly Ala Ala His Gln Ser Pro Glu Ser Leu
        35                  40                  45
Leu Gln Leu Lys Ala Leu Lys Pro Gly Val Ile Gln Ile Leu Gly Val
    50                  55                  60
Lys Thr Ser Arg Phe Leu Cys Gln Arg Pro Asp Gly Ala Leu Tyr Gly
65                  70                  75                  80
Ser Leu His Phe Asp Pro Glu Ala Cys Ser Phe Arg Glu Leu Leu Leu
                85                  90                  95
Glu Asn Gly Tyr Asn Val Tyr Gln Ser Glu Thr His Gly Leu Pro Leu
            100                 105                 110
His Leu Pro Cys Asn Lys Ser Pro His Arg Asp Pro Ala Ser Gln Gly
        115                 120                 125
Pro Ala Arg Phe Leu Pro Leu Pro Gly Leu Pro Pro Ala Pro Pro Glu
    130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Ala Arg Ser Pro Ser Tyr Ala
                165                 170                 175
```

Ser

<210> SEQ ID NO 36
<211> LENGTH: 177
<212> TYPE: PRT
<213> ORGANISM: Homo sapiens

<400> SEQUENCE: 36

```
Asp Ser Ser Pro Leu Leu Gln Phe Gly Gly Gln Val Arg Gln Arg Tyr
1               5                   10                  15

Leu Tyr Thr Asp Asp Ala Cys Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Gln Leu Lys Ala Leu Lys Pro Gly Val Ile Gln Ile Leu Gly Val
    50                  55                  60

Lys Thr Ser Arg Phe Leu Cys Gln Arg Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Cys Asn Arg Ser Pro His Arg Asp Pro Ala Ser Arg Gly
        115                 120                 125

Pro Ala Arg Phe Leu Pro Leu Pro Gly Leu Pro Pro Ala Pro Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser
```

<210> SEQ ID NO 37
<211> LENGTH: 177
<212> TYPE: PRT
<213> ORGANISM: Homo sapiens

<400> SEQUENCE: 37

```
Asp Ser Ser Pro Leu Leu Gln Phe Gly Gly Gln Val Arg Gln Arg Tyr
1               5                   10                  15

Leu Tyr Thr Asp Asp Ala Cys Gln Thr Glu Ala His Leu Glu Ile Arg
            20                  25                  30

Glu Asp Gly Thr Val Gly Gly Ala Ala Asp Gln Ser Pro Glu Ser Leu
        35                  40                  45

Leu Gln Leu Lys Ala Leu Lys Pro Gly Val Ile Gln Ile Leu Gly Val
    50                  55                  60

Lys Thr Ser Arg Phe Leu Cys Gln Arg Pro Asp Gly Thr Leu Tyr Gly
65                  70                  75                  80

Ser Leu His Phe Asp Pro Glu Ala Cys Ser Phe Arg Glu Leu Leu Leu
                85                  90                  95

Glu Asn Gly Tyr Asn Val Tyr Gln Ser Glu Thr His Gly Leu Pro Leu
            100                 105                 110

His Leu Pro Cys Asn Arg Ser Pro His Arg Asp Pro Ala Ser Arg Gly
        115                 120                 125

Pro Ala Arg Phe Leu Pro Leu Pro Gly Leu Pro Pro Ala Pro Pro Glu
    130                 135                 140
```

```
Pro Pro Gly Ile Leu Ala Pro Gln Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 38
<211> LENGTH: 177
<212> TYPE: PRT
<213> ORGANISM: Homo sapiens

<400> SEQUENCE: 38

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
                20                  25                  30

Glu Asp Gly Thr Val Gly Gly Ala Ala His Gln Ser Pro Glu Ser Leu
            35                  40                  45

Leu Glu Leu Lys Ala Leu Lys Pro Gly Val Ile Gln Ile Leu Gly Val
        50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Glu Gly Tyr Asn Val Tyr Gln Ser Glu Ala His Gly Leu Pro Leu
                100                 105                 110

His Leu Pro Gly Asn Arg Ser Pro His Arg Asp Pro Ala Pro Gln Gly
            115                 120                 125

Pro Ala Arg Phe Leu Pro Leu Pro Gly Leu Pro Pro Ala Leu Pro Glu
        130                 135                 140

Pro Pro Gly Ile Leu Ala Pro Gln Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 39
<211> LENGTH: 177
<212> TYPE: PRT
<213> ORGANISM: Homo sapiens

<400> SEQUENCE: 39

Asp Ser Ser Pro Leu Leu Gln Phe Gly Gly Gln Val Arg Gln Arg Tyr
1               5                   10                  15

Leu Tyr Thr Asp Asp Ala Gln Glu Thr Glu Ala His Leu Glu Ile Arg
                20                  25                  30

Glu Asp Gly Thr Val Gly Gly Ala Ala His Gln Ser Pro Glu Ser Leu
            35                  40                  45

Leu Glu Leu Lys Ala Leu Lys Pro Gly Val Ile Gln Ile Leu Gly Val
        50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
```

```
                100                 105                 110
His Leu Pro Gly Asn Arg Ser Pro His Cys Asp Pro Ala Pro Gln Gly
            115                 120                 125

Pro Ala Arg Phe Leu Pro Leu Pro Gly Leu Pro Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 40
<211> LENGTH: 177
<212> TYPE: PRT
<213> ORGANISM: Homo sapiens

<400> SEQUENCE: 40

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 41
<211> LENGTH: 177
<212> TYPE: PRT
<213> ORGANISM: Homo sapiens

<400> SEQUENCE: 41

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala Asp Gln Ser Pro Glu Ser Leu
        35                  40                  45

Leu Glu Leu Lys Ala Leu Lys Pro Gly Val Ile Gln Ile Leu Gly Val
    50                  55                  60
```

```
Lys Thr Ser Arg Phe Leu Cys Gln Lys Pro Asp Gly Thr Leu Tyr Gly
 65                  70                  75                  80

Ser Leu His Phe Asp Pro Glu Ala Cys Ser Phe Arg Glu Leu Leu Leu
                 85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser
```

<210> SEQ ID NO 42
<211> LENGTH: 177
<212> TYPE: PRT
<213> ORGANISM: Homo sapiens

<400> SEQUENCE: 42

```
Asp Ser Ser Pro Leu Leu Gln Phe Gly Gly Gln Val Arg Gln Arg Tyr
  1               5                  10                  15

Leu Tyr Thr Asp Asp Ala Gln Gln Thr Glu Ala His Leu Glu Ile Arg
             20                  25                  30

Glu Asp Gly Thr Val Gly Gly Ala Ala His Gln Ser Pro Glu Ser Leu
             35                  40                  45

Leu Glu Leu Lys Ala Leu Lys Pro Gly Val Ile Gln Ile Leu Gly Val
         50                  55                  60

Lys Thr Ser Arg Phe Leu Cys Gln Lys Pro Asp Gly Ala Leu Tyr Gly
 65                  70                  75                  80

Ser Leu His Phe Asp Pro Glu Ala Cys Ser Phe Arg Glu Leu Leu Leu
                 85                  90                  95

Glu Asp Gly Tyr Asn Val Tyr Gln Ser Glu Ala His Gly Leu Pro Leu
            100                 105                 110

His Leu Pro Gly Asn Arg Ser Pro His Cys Asp Pro Ala Ser Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser
```

<210> SEQ ID NO 43
<211> LENGTH: 177
<212> TYPE: PRT
<213> ORGANISM: Homo sapiens

<400> SEQUENCE: 43

```
Asp Ser Ser Pro Leu Leu Gln Phe Gly Gly Gln Val Arg Gln Arg Tyr
  1               5                  10                  15

Leu Tyr Thr Asp Asp Ala Gln Gln Thr Glu Ala His Leu Glu Ile Arg
             20                  25                  30
```

```
Glu Asp Gly Thr Val Gly Gly Ala Ala Asp Gln Ser Pro Glu Ser Leu
        35                  40                  45

Leu Glu Leu Lys Ala Leu Lys Pro Gly Val Ile Gln Ile Leu Gly Val
 50                  55                  60

Lys Thr Ser Arg Phe Leu Cys Gln Lys Pro Asp Gly Thr Leu Tyr Gly
 65                  70                  75                  80

Ser Leu His Phe Asp Pro Glu Ala Cys Ser Phe Arg Glu Leu Leu Leu
                 85                  90                  95

Glu Asp Gly Tyr Asn Val Tyr Gln Ser Glu Ala His Gly Leu Pro Leu
                100                 105                 110

His Leu Pro Gly Asn Arg Ser Pro His Cys Asp Pro Ala Ser Gln Gly
            115                 120                 125

Pro Ala Arg Phe Leu Pro Leu Pro Gly Leu Pro Pro Ala Leu Pro Glu
            130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 44
<211> LENGTH: 177
<212> TYPE: PRT
<213> ORGANISM: Homo sapiens

<400> SEQUENCE: 44

Asp Ser Ser Pro Leu Leu Gln Phe Gly Gly Gln Val Arg Gln Arg Tyr
 1               5                  10                  15

Leu Tyr Thr Asp Asp Ala Gln Gln Thr Glu Ala His Leu Glu Ile Arg
                 20                  25                  30

Glu Asp Gly Thr Val Gly Gly Ala Ala Asp Gln Ser Pro Glu Ser Leu
        35                  40                  45

Leu Glu Leu Lys Ala Leu Lys Pro Gly Val Ile Gln Ile Leu Gly Val
 50                  55                  60

Lys Thr Ser Arg Phe Leu Cys Gln Lys Pro Asp Gly Thr Leu Tyr Gly
 65                  70                  75                  80

Ser Leu His Phe Asp Pro Glu Ala Cys Ser Phe Arg Glu Leu Leu Leu
                 85                  90                  95

Glu Asp Gly Tyr Asn Val Tyr Gln Ser Glu Ala His Gly Leu Pro Leu
                100                 105                 110

His Leu Pro Gly Asn Arg Ser Pro His Cys Asp Pro Ala Ser Arg Gly
            115                 120                 125

Pro Ala Arg Phe Leu Pro Leu Pro Gly Leu Pro Pro Ala Leu Pro Glu
            130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 45
<211> LENGTH: 177
<212> TYPE: PRT
<213> ORGANISM: Homo sapiens
```

-continued

```
<400> SEQUENCE: 45

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala Asp Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Arg Pro Asp Gly Thr Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Thr His Gly Leu Pro Leu
            100                 105                 110

His Leu Pro Gly Asn Arg Ser Pro His Cys Asp Pro Ala Ser Arg Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Ala Arg Ser Pro Ser Tyr Ala
                165                 170                 175

Ser

<210> SEQ ID NO 46
<211> LENGTH: 177
<212> TYPE: PRT
<213> ORGANISM: Homo sapiens

<400> SEQUENCE: 46

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala His Gln Ser Pro Glu Ser Leu
        35                  40                  45

Leu Glu Leu Lys Ala Leu Lys Pro Gly Val Ile Gln Ile Leu Gly Val
    50                  55                  60

Lys Thr Ser Arg Phe Leu Cys Gln Lys Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Glu Gly Tyr Asn Val Tyr Gln Ser Glu Ala His Gly Leu Pro Leu
            100                 105                 110

His Leu Pro Gly Asn Arg Ser Pro His Cys Asp Pro Ala Pro Gln Gly
        115                 120                 125

Pro Ala Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser
```

<210> SEQ ID NO 47
<211> LENGTH: 546
<212> TYPE: DNA
<213> ORGANISM: Homo sapiens

<400> SEQUENCE: 47 cacccatcc ctgactccag tcctctcctg caattcgggg gccaagtccg gcagcggtac    60
ctctacacag atgatgccca gcagacagaa gcccacctgg agatcaggga ggatgggacg   120
gtgggggcg ctgctgacca gagccccgaa agtctcctgc agctgaaagc cttgaagccg   180
ggagttattc aaatcttggg agtcaagaca tccaggttcc tgtgccagcg gccagatggg   240
gccctgtatg gatcgctcca ctttgaccct gaggcctgca gcttccggga gctgcttctt   300
gaggacggat acaatgttta ccagtccgaa gcccacggcc tcccgctgca cctgccaggg   360
aacaagtccc cacaccggga ccctgcaccc cgaggaccag ctcgcttcct gccactacca   420
ggcctgcccc ccgcactccc ggagccaccc ggaatcctgg cccccagcc cccgatgtg    480
ggctcctcgg accctctgag catggtggga ccttcccagg gccgaagccc cagctacgct   540
tcctga                                                              546

<210> SEQ ID NO 48
<211> LENGTH: 177
<212> TYPE: PRT
<213> ORGANISM: Homo sapiens

<400> SEQUENCE: 48

Asp Ser Ser Pro Leu Leu Gln Phe Gly Gly Gln Val Arg Gln Arg Tyr
 1               5                  10                  15

Leu Tyr Thr Asp Asp Ala Gln Gln Thr Glu Ala His Leu Glu Ile Arg
            20                  25                  30

Glu Asp Gly Thr Val Gly Gly Ala Ala Asp Gln Ser Pro Glu Ser Leu
        35                  40                  45

Leu Gln Leu Arg Ala Leu Arg Pro Gly Val Ile Gln Ile Leu Gly Val
    50                  55                  60

Arg Thr Ser Arg Phe Leu Cys Gln Arg Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Leu Pro Gly Asn Arg Ser Pro His Lys Asp Pro Ala Pro Arg Gly
        115                 120                 125

Pro Ala Arg Phe Leu Pro Leu Pro Gly Leu Pro Pro Ala Pro Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 49
<211> LENGTH: 177
<212> TYPE: PRT
<213> ORGANISM: Homo sapiens

<400> SEQUENCE: 49

```
Asp Ser Ser Pro Leu Leu Gln Phe Gly Gly Gln Val Arg Gln Arg Tyr
 1           5                   10                  15
Leu Tyr Thr Asp Asp Ala Cys Gln Thr Glu Ala His Leu Glu Ile Arg
            20                  25                  30
Glu Asp Gly Thr Val Gly Gly Ala Ala Asp Gln Ser Pro Glu Ser Leu
        35                  40                  45
Leu Gln Leu Arg Ala Leu Arg Pro Gly Val Ile Gln Ile Leu Gly Val
    50                  55                  60
Arg Thr Ser Arg Phe Leu Cys Gln Arg Pro Asp Gly Ala Leu Tyr Gly
65                      70                  75                  80
Ser Leu His Phe Asp Pro Glu Ala Cys Ser Phe Arg Glu Leu Leu Leu
                85                  90                      95
Glu Asp Gly Tyr Asn Val Tyr Gln Ser Glu Ala His Gly Leu Pro Leu
            100                 105                 110
His Leu Pro Cys Asn Arg Ser Pro His Lys Asp Pro Ala Pro Arg Gly
        115                 120                 125
Pro Ala Arg Phe Leu Pro Leu Pro Gly Leu Pro Pro Ala Pro Pro Glu
    130                 135                 140
Pro Pro Gly Ile Leu Ala Pro Gln Pro Pro Asp Val Gly Ser Ser Asp
145                 150                 155                 160
Pro Leu Ala Met Val Gly Pro Ser Gln Gly Arg Ser Pro Ser Tyr Ala
                165                 170                 175
Ser
```

FIBROBLAST GROWTH FACTOR 21 MUTATIONS

FIELD OF THE INVENTION

The present invention relates to new polypeptide of fibroblast growth factor 21 (FGF21) that have improved pharmaceutical properties. Also disclosed are methods for treating FGF21-associated disorders, such as obesity, type 1 and type 2 diabetes mellitus, pancreatitis, dyslipidemia, nonalcoholic steatohepatitis (NASH), insulin resistance, hyperinsulinemia, glucose intolerance, hyperglycemia, metabolic syndrome, and other metabolic disorders, and in reducing the mortality and morbidity of critically ill patients.

BACKGROUND OF THE INVENTION

The fibroblast growth factor (FGF) family is characterized by 22 genetically distinct, homologous ligands, which are grouped into seven subfamilies. According to the published literature, the FGF family now consists of at least twenty-three members, FGF-1 to FGF-23 (Reuss et al., Cell Tissue Res. 313:139-157 (2003).

FGF-21 was isolated from mouse embryos and is closest to FGF-19 and FGF-23. This FGF subfamily regulates diverse physiological processes uncommon to classical FGFs, namely energy and bile acid homeostasis, glucose and lipid metabolism and phosphate as well as vitamin D homeostasis. Moreover, unlike classical FGFs, this subfamily acts in an endocrine fashion. (Moore, D. D. (2007) Science 316, 1436-8). Fibroblast growth factor 21 (FGF21) has been reported to be preferentially expressed in the liver (Nishimura et al., Biochimica et Biophysica Acta, 1492:203-206, (2000); patent publication WO01/36640; and patent publication WO01/18172) and described as a treatment for ischemic vascular disease, wound healing, and diseases associated with loss of pulmonary, bronchia or alveolar cell function and numerous other disorders.

FGF21 has been identified as a potent metabolic regulator. Systemic administration of FGF21 to rodents and rhesus monkeys with diet-induced or genetic obesity and diabetes exerts strong anti-hyperglycemic and triglyceride-lowering effects, and reduction of body weight. (Coskun, T, et al. (2008) Endocrinology 149:6018-6027; Kharitonenkov, A, et al. (2005) Journal of Clinical Investigation 115:1627-1635; Kharitonenkov, A, et al. (2007) Endocrinology 148:774-781; Xu, J, et al. (2009) Diabetes 58:250-259). FGF21 is a 209 amino acid polypeptide containing a 28 amino acid leader sequence. Human FGF21 has about 79% amino acid identity to mouse FGF21 and about 80% amino acid identity to rat FGF21.

Although FGF-21 activates FGF receptors and downstream signaling molecules, including FRS2a and ERK, direct interaction of FGFRs and FGF-21 has not been detected. Furthermore, various non-adipocyte cells do not respond to FGF-21, even though they express multiple FGFR isoforms. All of these data suggest that a cofactor must mediate FGF-21 signaling through FGFRs. Recent studies have identified β-klotho, which is highly expressed in liver, adipocytes and in pancreas, as a determinant of the cellular response to FGF-21 (Kurosu, H. et al. (2007) J Biol Chem 282, 26687-95). (3-klotho preferentially binds to FGFR1c and FGFR4. The β-klotho-FGFR complex, but not FGFR alone, binds to FGF-21 in vitro (Kharitonenkov, A. et al. (2008) J Cell Physiol 215, 1-7). A similar mechanism has been identified in the FGF-23-klotho-FGFR system (Urakawa, I. et al. (2006) Nature 444, 770-4).

The bioactivity of FGF-21 was first identified in a mouse 3T3-L1 adipocyte glucose uptake assay (Kharitonenkov, A. et al. (2005) J Clin Invest 115, 1627-35). Subsequently, FGF-21 was shown to induce insulin-independent glucose uptake and GLUT1 expression. FGF-21 has also been shown to ameliorate hyperglycemia in a range of diabetic rodent models. In addition, transgenic mice over-expressing FGF-21 were found to be resistant to diet-induced metabolic abnormalities, including decreased body weight and fat mass, and enhancements in insulin sensitivity (Badman, M. K. et al. (2007) Cell Metab 5, 426-37). Administration of FGF-21 to diabetic non-human primates caused a decline in fasting plasma glucose, triglycerides, insulin and glucagon levels, and led to significant improvements in lipoprotein profiles including a nearly 80% increase in HDL cholesterol (Kharitonenkov, A. et al. (2007) Endocrinology 148, 774-81). Importantly, hypoglycemia was not observed at any point during this NHP study. Moreover, recent studies identified FGF-21 as an important endocrine hormone that helps to control adaptation to the fasting state. This provides a previously missing link, downstream of PPARα, by which the liver communicates with the rest of the body in regulating the biology of energy homeostasis.

The combined observations that FGF-21 regulates adipose (lipolysis), liver (fatty acid oxidation and ketogenesis), and brain (torpor) establish it as a major endocrine regulator of the response to fasting (Kharitonenkov, A. & Shanafelt, A. B. (2008) BioDrugs 22, 37-44). However, the problem with using FGF-21 directly as a biotherapeutic is that its half-life is very short. In mice, the half-life of human FGF21 is 0.5 to 1 hours, and in cynomolgus monkeys, the half-life is 2 to 3 hours.

In developing an FGF21 protein for use as a therapeutic in the treatment of type 1 and type 2 diabetes mellitus and other metabolic conditions, an increase in half-life and stability would be desirable. FGF21 proteins having enhanced half-life and stability would allow for less frequent dosing of patients being administered the protein. Clearly, there is a need to develop a stable aqueous protein formulation for the therapeutic protein FGF21.

FGF21 may be utilized as a multi-use, sterile pharmaceutical formulation. However, it has been determined that preservatives, i.e., m-cresol, have an adverse affect on its stability under these conditions. The present invention overcomes the significant hurdles of physical instabilities with the invention of variants of FGF21 that are more stable, less susceptible to proteolysis and enzymatic degradation, and less likely to aggregate and form complexes, than wild-type FGF21 under pharmaceutical formulation conditions.

Thus, the variants of FGF21 of the present invention provide stable pharmacological protein formulations that are useful for the treatment of FGF21-associated disorders, such as obesity, type 2 diabetes mellitus, type 1 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders, and in reducing the mortality and morbidity of critically ill patients.

SUMMARY OF THE INVENTION

The invention relates to the identification of new polypeptide and protein variants of fibroblast growth factor 21 (FGF21) that have improved pharmaceutical properties, e.g., are more stable, less susceptible to proteolysis and enzymatic degradation, and less likely to aggregate and form complexes, than wild-type FGF21 under pharmaceutical formulation conditions. Also disclosed are methods for treating FGF21-associated disorders, including metabolic conditions.

The FGF21 protein variants of the present invention may be used as a once weekly injectable either alone or in combination with oral anti-diabetic agents which will improve the glycemic control, body weight and lipid profile of type 1 and type 2 diabetes mellitus patients. In a first aspect, the invention provides polypeptide and protein variants of Fibroblast Growth Factor 21 (FGF21), which include but are not limited to one or more of the sequences listed in Table 1, and further described herein. Said FGF21 variants of Table 1 comprise 4 amino acid N-terminally truncated mature FGF21 wild-type proteins (i.e., 4 residue N-terminal truncated versions of the mature FGF21 sequence (SEQ ID NO:3)) with a variety of site-specific internal modifications. The variants of Table 1 are numbered relative to the full length FGF21 protein sequence (NCBI reference sequence number NP_061986.1); for example, the aspartic acid residue in position one of Variant 1 (SEQ ID NO:5) corresponds to residue number 33 of SEQ ID NO:1 (and residue number 5 of mature FGF21 sequence (SEQ ID NO:3)).

TABLE 1

List of FGF21 variants, amino acid sequences and amino acid changes relative to wild type FGF21 (SEQ ID NO: 1).

| Variant | SEQ ID NO: | Sequence | Site-specific modifications made relative to prior art SEQ ID NO: 1 (full length FGF21 protein sequence (NCBI reference sequence number NP_061986.1)) |
|---|---|---|---|
| 1 | 5 | DSSPLLQFGG QVRQRYLYTD DAQETEAHLE IREDGTAGGA ADQSPESLLE LKALKPGVIQ ILGVKTSRFL CQGPDGALYG SLHFDPEACS FRELVLEDGY NVYQSEAHGL PLHLPGHKSP HRDPAPRGPA RFLPLPGLPP ALPEPPGILA PEPPDVGSSD PLSMVGPSQG RSPSYTS | Q56E, V69A, Q82E, R105G, L127V, N149H, Q184E, A208T |
| 2 | 6 | DSSPLLQFGG QVRQRYLYTD DAQNTEAHLE IREDGTAGGA ADQSPESLLN LKALKPGVIQ ILGVKTSRFL CQKPDGALYG SLHFDPEACS FRELVLEDGY NVYQSEAHGL PLHLPGQKSP HRDPAPRGPA RFLPLPGLPP ALPEPPGILA PNPPDVGSSD PLSMVGPSQG RSPSYTS | Q56N, V69A, Q82N, R105K, L127V, N149Q, Q184N, A208T |
| 5 | 7 | DSSPLLQFGG QVRQRYLYTD DDQQTEAHLE IREDGTVGGA AHQSPESLLQ LKALKPGVIQ ILGVKASRFL CQKPDGALYG SLHFDPEACS FRELLLENGY NVYQSEAHGL PLHLPGNRSP HRDPASQGPA RFLPLPGLPP ALPEPPGILA PQPPDVGSSD PLAMVGPSQA RSPSYAS | A54D, D74H, T98A, R105K, D130N, K150R, P158S, R159Q, S195A, G202A |
| 6 | 8 | DSSPLLQFGG QVRQRYLYTD DDQQTEAHLE IREDGTVGGA AHQSPESLLQ LKALKPGVIQ ILGVQTSRFL CQKPDGALYG SLHFDPEACS FRELLLENGY NVYQSETHGL PLHLPGNKSP HRDPASQGPA RFLPLPGLPP ALPEPPGILA PQPPDVGSSD PLAMVGPSQA RSPSYAS | A54D, D74H, K97Q, R105K, D130N, A139T, P158S, R159Q, S195A, G202A |
| 7 | 9 | DSSPLLQFGG QVRQRYLYTD DAQETEAHLE IREDGTVGGA AHQSPESLLQ LKALKPGVIQ ILGVKASRFL CQKPDGALYG SLHFDPEACS FRELLLENGY NVYQSEAHGL PLHLPGNRSP HRDPASQGPA RFLPLPGLPP ALPEPPGILA PQPPDVGSSD PLAMVGPSQA RSPSYAS | Q56E, D74H, T98A, R105K, D130N, K150R, P158S, R159Q, S195A, G202A |
| 8 | 10 | DSSPLLQFGG QVRQRYLYTD DAQETEAHLE IREDGTVGGA AHQSPESLLQ LKALKPGVIQ ILGVQTSRFL CQKPDGALYG SLHFDPEACS FRELLLENGY NVYQSETHGL PLHLPGNKSP HRDPASQGPA RFLPLPGLPP ALPEPPGILA PQPPDVGSSD PLAMVGPSQA RSPSYAS | Q56E, D74H, K97Q, R105K, D130N, A139T, P158S, R159Q, S195A, G202A |
| 9 | 11 | DSSPLLQFGG QVRQRYLYTD DDQQTEAHLE IREDGTVGGA AHQSPESLLQ LKALKPGVIQ ILGVKASRFL CQKPDGALYG SLHFDPEACS FRELLLENGY NVYQSETHGL PLHLPGNKSP HRDPASQGPA RFLPLPGLPP ALPEPPGILA PQPPDVGSSD PLAMVGPSQA RSPSYAS | A54D, D74H, T98A, R105K, D130N, A139T, P158S, R159Q, S195A, G202A |
| 10 | 12 | DSSPLLQFGG QVRQRYLYTD DAQETEAHLE IREDGTVGGA AHQSPESLLQ LKALKPGVIQ ILGVKASRFL CQKPDGALYG SLHFDPEACS FRELLLENGY NVYQSETHGL PLHLPGNKSP | Q56E, D74H, T98A, R105K, D130N, A139T, P158S, R159Q, S195A, G202A |

TABLE 1-continued

List of FGF21 variants, amino acid sequences and amino acid changes relative to wild type FGF21 (SEQ ID NO: 1).

| Variant | SEQ ID NO: | Sequence | Site-specific modifications made relative to prior art SEQ ID NO: 1 (full length FGF21 protein sequence (NCBI reference sequence number NP_061986.1)) |
|---|---|---|---|
| | | HRDPASQGPA RFLPLPGLPP ALPEPPGILA PQPPDVGSSD PLAMVGPSQA RSPSYAS | |
| 11 | 13 | DSSPLLQFGG QVRQRYLYTD DDQQTEAHLE IREDGTVGGA AHQSPESLLE LKALKPGVIQ ILGVKTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | A54D, D74H, Q82E, R105K, D130N, K150R, R159Q, S195A |
| 12 | 14 | DSSPLLQFGG QVRQRYLYTD DDQQTEAHLE IREDGTVGGA AHQSPESLLQ LKALKPGVIQ ILGVQTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | A54D, D74H, K97Q, R105K, D130N, K150R, R159Q, S195A |
| 13 | 15 | DSSPLLQFGG QVRQRYLYTD DDQQTEAHLE IREDGTVGGA AHQSPESLLQ LKALKPGVIQ ILGVKASRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | A54D, D74H, T98A, R105K, D130N, K150R, R159Q, S195A |
| 14 | 16 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | Q56E, D74H, Q82E, R105K, D130N, K150R, R159Q, S195A |
| 14-R15C, L174P | 17 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLENGY NVYQSEAHGL PLHLPGNRSP HCDPAPQGPA RFLPLPGLPP APPEPPGILA PQPPDVGSSD PLAMVGPSQG RSPSYAS | Q56E, D74H, Q82E, R105K, D130N, K150R, R154C, R159Q, L174P, S195A |
| 15 | 18 | DSSPLLQFGG QVRQRYLYTD DAQETEAHLE IREDGTVGGA AHQSPESLLQ LKALKPGVIQ ILGVQTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | Q56E, D74H, K97Q, R105K, D130N, K150R, R159Q, S195A |
| 16 | 19 | DSSPLLQFGG QVRQRYLYTD DAQETEAHLE IREDGTVGGA AHQSPESLLQ LKALKPGVIQ ILGVKASRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | Q56E, D74H, T98A, R105K, D130N, K150R, R159Q, S195A |
| 17 | 20 | DSSPLLQFGG QVRQRYLYTD DAQQTESHLE IREDGTVGGA AHQSPESLLE LKALKPGVIQ ILGVKTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | A59S, D74H, Q82E, R105K, D130N, K150R, R159Q, S195A |
| 18 | 21 | DSSPLLQFGG QVRQRYLYTD DAQQTESHLE IREDGTVGGA AHQSPESLLQ LKALKPGVIQ ILGVQTSRFL CQKPDGALYG SLHFDPEACS FRELLLENGY NVYQSEAHGL PLHLPGNRSP HRDPAPQGPA RFLPLPGLPP ALPEPPGILA PQPPDVGSSD PLAMVGPSQG RSPSYAS | A59S, D74H, K97Q, R105K, D130N, K150R, R159Q, S195A |
| 19 | 22 | DSSPLLQFGG QVRQRYLYTD DAQQTESHLE IREDGTVGGA AHQSPESLLQ LKALKPGVIQ ILGVKASRFL CQKPDGALYG SLHFDPEACS | A59S, D74H, T98A, R105K, D130N, K150R, R159Q, S195A |

TABLE 1-continued

List of FGF21 variants, amino acid sequences and amino acid changes relative to wild type FGF21 (SEQ ID NO: 1).

| Variant | SEQ ID NO: | Sequence | Site-specific modifications made relative to prior art SEQ ID NO: 1 (full length FGF21 protein sequence (NCBI reference sequence number NP_061986.1)) |
|---|---|---|---|
| | | FRELLLENGY NVYQSEAHGL PLHLPGNRSP HRDPAPQGPA RFLPLPGLPP ALPEPPGILA PQPPDVGSSD PLAMVGPSQG RSPSYAS | |
| 50 | 23 | DSSPLLQFGG QVRQRYLYTD DDQQTEAHLE IREDGTVGGA AHQSPESLLQ LKALKPGVIQ ILGVQTSRFL CQKPDGALYG SLHFDPEACS FRELLLENGY NVYQSEAHGL PLHLPGNRSP HRDPASQGPA RFLPLPGLPP ALPEPPGILA PQPPDVGSSD PLAMVGPSQA RSPSYAS | A54D, D74H, K97Q, R105K, D130N, K150R, P158S, R159Q, S195A, G202A |
| 51 | 24 | DSSPLLQFGG QVRQRYLYTD DAQETEAHLE IREDGTVGGA AHQSPESLLQ LKALKPGVIQ ILGVQTSRFL CQKPDGALYG SLHFDPEACS FRELLLENGY NVYQSEAHGL PLHLPGNRSP HRDPASQGPA RFLPLPGLPP ALPEPPGILA PQPPDVGSSD PLAMVGPSQA RSPSYAS | Q56E, D74H, K97Q, R105K, D130N, K150R, P158S, R159Q, S195A, G202A |
| 52 | 25 | DSSPLVQFGG QVRQRYLYTD DAQQTEAHLE IREDGTVGGA AHQSPESLLQ LKALKPGVIQ ILGVKTSRFL CQKPDGALYG SLHFDPEACS FRELLLENGY NVYQSEAHSL PLHLPGNKSP HRDPASQGPA RFLPLPGLPP ALPEPPGILA PQPPDVGSSD PLSMVGPSQA RSPSYAS | L38V, D74H, R105K, D130N, G141S, P158S, R159Q, G202A |
| 53 | 26 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLENGY NVYQSEAHGL PLHLPGNRSP HRDPASQGPA RFLPLPGLPP APPEPPGILA PQPPDVGSSD PLAMVGPSQG RSPSYAS | Q56E, D74H, Q82E, R105K, D130N, K150R, P158S, R159Q, L174P, S195A |
| 54 | 27 | DSSPLLQFGG QVRQRYLYTD DAQQTEAHLE IREDGTVGGA AHQSPESLLE LKALKPGVIQ ILGVKTSRFL CQKPDGTLYG SLHFDPEACS FRELLLENGY NVYQSEAHGL PLHLPGNRSP HRDPASQGPA RFLPLPGLPP APPEPPGILA PQPPDVGSSD PLAMVGPSQG RSPSYAS | D74H, Q82E, R105K, A109T, D130N, K150R, P158S, R159Q, L174P, S195A |
| 55 | 28 | DSSPLLQFGG QVRQRYLYTD DAQQTEAHLE IREDGTAGGA AHQSPESLLE LKALKPGVIQ ILGVKTSRFL CQKPDGALYG SLHFDPEACS FRELLLENGY NVYQSEAHGL PLHLPGNRSP HRDPASQGPA RFLPLPGLPP APPEPPGILA PQPPDVGSSD PLAMVGPSQG RSPSYAS | V69A, D74H, Q82E, R105K, D130N, K150R, P158S, R159Q, L174P, S195A |
| 56 | 29 | DSSPLLQFGG QVRQRYLYTD DAQQTEAHLE IREDGTVGGA AHQSPESLLQ LKALKPGVIQ ILGVKASRFL CQKPDGALYG SLHFDPEACS FRELLLENGY NVYQSETHGL PLHLPGNKSP HRDPASQGPA RFLPLPGLPP APPEPPGILA PQPPDVGSSD PLAMVGPSQA RSPSYAS | D74H, T98A, R105K, D130N, A139T, P158S, R159Q, L174P, S195A, G202A |
| 57 | 30 | DSSPLLQFGG QVRQRYLYTD DAQQTEAHLE IREDGTVGGA AHQSPESLLQ LKALKPGVIQ ILGVKASRFL CQRPDGALYG SLHFDPEACS FRELLLENGY NVYQSETHGL PLHLPGNRSP HRDPASQGPA RFLPLPGLPP APPEPPGILA PQPPDVGSSD PLAMVGPSQA RSPSYAS | D74H, T98A, D130N, A139T, K150R, P158S, R159Q, L174P, S195A, G202A |
| 58 | 31 | DSSPLLQFGG QVRQRYLYTD DAQQTEAHLE IREDGTVGGA AHQSPESLLQ LKALKPGVIQ ILGVKTSRFL CQRPDGTLYG SLHFDPEACS FRELLLENGY NVYQSETHGL PLHLPGNRSP HRDPASQGPA RFLPLPGLPP APPEPPGILA PQPPDVGSSD PLAMVGPSQA RSPSYAS | D74H, A109T, D130N, A139T, K150R, P158S, R159Q, L174P, S195A, G202A |
| 59 | 32 | DSSPLLQFGG QVRQRYLYTD DACQTEAHLE IREDGTVGGA AHQSPESLLE LKALKPGVIQ | Q55C, D74H, Q82E, D130N, G148C, K150R, P158S, |

TABLE 1-continued

List of FGF21 variants, amino acid sequences and amino acid changes relative to wild type FGF21 (SEQ ID NO: 1).

| Variant | SEQ ID NO: | Sequence | Site-specific modifications made relative to prior art SEQ ID NO: 1 (full length FGF21 protein sequence (NCBI reference sequence number NP_061986.1)) |
|---|---|---|---|
| | | ILGVKTSRFL CQRPDGALYG SLHFDPEACS FRELLLENGY NVYQSEAHGL PLHLPCNRSP HRDPASQGPA RFLPLPGLPP APPEPPGILA PQPPPDVGSSD PLAMVGPSQG RSPSYAS | R159Q, L174P, S195A |
| 60 | 33 | DSSPLLQFGG QVRQRYLYTD DACQTEAHLE IREDGTVGGA AHQSPESLLE LKALKPGVIQ ILGVKTSRFL CQRPDGTLYG SLHFDPEACS FRELLLENGY NVYQSEAHGL PLHLPCNRSP HRDPASRGPA RFLPLPGLPP APPEPPGILA PQPPPDVGSSD PLAMVGPSQG RSPSYAS | Q55C, D74H, Q82E, A109T, D130N, G148C, K150R, P158S, L174P, S195A |
| 61 | 34 | DSSPLLQFGG QVRQRYLYTD DACQTEAHLE IREDGTAGGA AHQSPESLLE LKALKPGVIQ ILGVKTSRFL CQRPDGALYG SLHFDPEACS FRELLLENGY NVYQSEAHGL PLHLPCNRSP HRDPASRGPA RFLPLPGLPP APPEPPGILA PQPPPDVGSSD PLAMVGPSQG RSPSYAS | Q55C, V69A, D74H, Q82E, D130N, G148C, K150R, P158S, L174P, S195A |
| 62 | 35 | DSSPLLQFGG QVRQRYLYTD DACQTEAHLE IREDGTVGGA AHQSPESLLQ LKALKPGVIQ ILGVKTSRFL CQRPDGALYG SLHFDPEACS FRELLLENGY NVYQSETHGL PLHLPCNKSP HRDPASQGPA RFLPLPGLPP APPEPPGILA PQPPPDVGSSD PLAMVGPSQA RSPSYAS | Q55C, D74H, D130N, A139T, G148C, P158S, R159Q, L174P, S195A, G202A |
| 63 | 36 | DSSPLLQFGG QVRQRYLYTD DACQTEAHLE IREDGTVGGA AHQSPESLLQ LKALKPGVIQ ILGVKTSRFL CQRPDGALYG SLHFDPEACS FRELLLENGY NVYQSETHGL PLHLPCNRSP HRDPASRGPA RFLPLPGLPP APPEPPGILA PQPPPDVGSSD PLAMVGPSQA RSPSYAS | Q55C, D74H, D130N, A139T, G148C, K150R, P158S, L174P, S195A, G202A |
| 64 | 37 | DSSPLLQFGG QVRQRYLYTD DACQTEAHLE IREDGTVGGA ADQSPESLLQ LKALKPGVIQ ILGVKTSRFL CQRPDGTLYG SLHFDPEACS FRELLLENGY NVYQSETHGL PLHLPCNRSP HRDPASRGPA RFLPLPGLPP APPEPPGILA PQPPPDVGSSD PLAMVGPSQA RSPSYAS | Q55C, A109T, D130N, A139T, G148C, K150R, P158S, L174P, S195A, G202A |
| 73 | 38 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEEGY NVYQSEAHGL PLHLPGNRSP HRDPAPQGPA RFLPLPGLPP ALPEPPGILA PQPPPDVGSSD PLAMVGPSQG RSPSYAS | Q56E, D74H, Q82E, R105K, D130E, K150R, R159Q, S195A |
| 76 | 39 | DSSPLLQFGG QVRQRYLYTD DAQETEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPPDVGSSD PLAMVGPSQG RSPSYAS | Q56E, D74H, Q82E, R105K, K150R, R154C, R159Q, S195A |
| 79 | 40 | DSSPLLQFGG QVRQRYLYTD DAQQTEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPAPQGPA RFLPLPGLPP ALPEPPGILA PQPPPDVGSSD PLAMVGPSQA RSPSYAS | D74H, Q82E, R105K, K150R, R154C, R159Q, S195A, G202A |
| 80 | 41 | DSSPLLQFGG QVRQRYLYTD DAQQTEAHLE IREDGTVGGA ADQSPESLLE LKALKPGVIQ ILGVKTSRFL CQKPDGTLYG SLHFDPEACS FRELLLEDGY NVYQSEAHGL PLHLPGNRSP HCDPAPQGPA RFLPLPGLPP ALPEPPGILA PQPPPDVGSSD PLAMVGPSQA RSPSYAS | Q82E, R105K, A109T, K150R, R154C, R159Q, S195A, G202A |

TABLE 1-continued

List of FGF21 variants, amino acid sequences and amino acid changes relative to wild type FGF21 (SEQ ID NO: 1).

| Variant | SEQ ID NO: | Sequence | Site-specific modifications made relative to prior art SEQ ID NO: 1 (full length FGF21 protein sequence (NCBI reference sequence number NP_061986.1)) |
|---|---|---|---|
| 81 | 42 | DSSPLLQFGG QVRQRYLYTD DAQQTEAHLE IREDGTVGGA AHQSPESLLE LKALKPGVIQ ILGVKTSRFL CQKPDGALYG SLHFDPEACS FRELLLEDGY NVYQSEAHGL PLHLPGNRSP HCDPASQGPA RFLPLPGLPP ALPEPPGILA PQPPDVGSSD PLAMVGPSQG RSPSYAS | D74H, Q82E, R105K, K150R, R154C, P158S, R159Q, S195A |
| 82 | 43 | DSSPLLQFGG QVRQRYLYTD DAQQTEAHLE IREDGTVGGA ADQSPESLLE LKALKPGVIQ ILGVKTSRFL CQKPDGTLYG SLHFDPEACS FRELLLEDGY NVYQSEAHGL PLHLPGNRSP HCDPASQGPA RFLPLPGLPP ALPEPPGILA PQPPDVGSSD PLAMVGPSQG RSPSYAS | Q82E, R105K, A109T, K150R, R154C, P158S, R159Q, S195A |
| 83 | 44 | DSSPLLQFGG QVRQRYLYTD DAQQTEAHLE IREDGTVGGA ADQSPESLLE LKALKPGVIQ ILGVKTSRFL CQKPDGTLYG SLHFDPEACS FRELLLEDGY NVYQSEAHGL PLHLPGNRSP HCDPASRGPA RFLPLPGLPP ALPEPPGILA PQPPDVGSSD PLAMVGPSQA RSPSYAS | Q82E, R105K, A109T, K150R, R154C, P158S, S195A, G202A |
| 84 | 45 | DSSPLLQFGG QVRQRYLYTD DAQQTEAHLE IREDGTVGGA ADQSPESLLE LKALKPGVIQ ILGVKTSRFL CQRPDGTLYG SLHFDPEACS FRELLLEDGY NVYQSETHGL PLHLPGNRSP HCDPASRGPA RFLPLPGLPP ALPEPPGILA PQPPDVGSSD PLAMVGPSQA RSPSYAS | Q82E, A109T, A139T, K150R, R154C, P158S, S195A, G202A |
| 85 | 46 | DSSPLLQFGG QVRQRYLYTD DAQQTEAHLE IREDGTVGGA AHQSPESLLE LKALKPGVIQ ILGVKTSRFL CQKPDGALYG SLHFDPEACS FRELLLEEGY NVYQSEAHGL PLHLPGNRSP HCDPAPQGPA RFLPLPGLPP ALPEPPGILA PQPPDVGSSD PLAMVGPSQG RSPSYAS | D74H, Q82E, R105K, D130E, K150R, R154C, R159Q, S195A |
| 86 | 48 | DSSPLLQFGG QVRQRYLYTD DAQQTEAHLE IREDGTVGGA ADQSPESLLQ LRALRPGVIQ ILGVRTSRFL CQRPDGALYG SLHFDPEACS FRELLLEDGY NVYQSEAHGL PLHLPGNRSP HKDPAPRGPA RFLPLPGLPP APPEPPGILA PQPPDVGSSD PLAMVGPSQG RSPSYAS | K84R, K87R, K97R, K150R, R154K, L174P, S195A |
| 87 | 49 | DSSPLLQFGG QVRQRYLYTD DACQTEAHLE IREDGTVGGA ADQSPESLLQ LRALRPGVIQ ILGVRTSRFL CQRPDGALYG SLHFDPEACS FRELLLEDGY NVYQSEAHGL PLHLPCNRSP HKDPAPRGPA RFLPLPGLPP APPEPPGILA PQPPDVGSSD PLAMVGPSQG RSPSYAS | Q55C, K84R, K87R, K97R, G148C, K150R, R154K, L174P, S195A |

Other embodiments are drawn to polynucleotides encoding the polypeptide and protein variants of the invention, a vector containing said polynucleotides and a host cell carrying said vector.

Provided herein are methods used to generate said polypeptides and protein variants, wherein such methods involve modification of the wild-type FGF21 protein, via e.g., truncations of the wild-type FGF21 protein, and the site-specific incorporation of amino acids at positions of interest within the wild-type FGF21 protein. Said modifications enhance the biological properties of the variants of the invention relative to the wild-type FGF21 protein, as well as, in some cases, serving as points of attachment for, e.g., labels and protein half-life extension agents, and for purposes of affixing said variants to the surface of a solid support. Related embodiments of the invention are methods of produce cells capable of producing said polypeptide and protein variants, and of producing vectors containing DNA encoding said variants.

In various embodiments, the polypeptide and protein variants disclosed herein can comprise (a) an amino-terminal truncation of no more than 8 amino acid residues, wherein the polypeptide is capable of lowering blood glucose in a mammal; (b) a carboxyl-terminal truncation of no more than 12 amino acid residues, wherein the polypeptide is capable of lowering blood glucose in a mammal; or (c) an amino-terminal truncation of no more than 8 amino acid residues and a carboxyl-terminal truncation of no more than 12 amino acid residues, wherein the polypeptide is capable of lowering blood glucose in a mammal.

In some embodiments, the polypeptide and protein variants disclosed herein can be covalently linked to one or more polymers, such as polyethylene glycol (PEG) or polysialic acid, whether at the position of site-specific amino acid modifications made relative to the wild-type FGF21, or at the position of amino acids commonly shared with the wild-type FGF21. In other embodiments, the polypeptides of the invention can be fused to a heterologous amino acid sequence, optionally via a linker, such as GS or GGGGSGGGGSGGGGS (SEQ ID NO:4). The heterologous amino acid sequence can be an IgG constant domain or fragment thereof (e.g., the Fc region), Human Serum Albumin (HSA), or albumin-binding polypeptides. Such fusion polypeptides disclosed herein can also form multimers.

In some embodiments, the fusion heterologous amino acid sequence (e.g., HSA, Fc, etc.) is fused to the amino-terminal of the protein variants of the invention. In other embodiments, the fusion heterologous amino acid sequence (e.g., HSA, Fc, etc.) is fused to the carboxyl-terminal of the protein variants of the invention.

Yet another embodiment is drawn to methods of treating a patient exhibiting one or more FGF21-associated disorders, such as obesity, type 2 diabetes mellitus, type 1 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders, comprising administering to said patient in need of such treatment a therapeutically effective amount of one or more human FGF21 polypeptide and protein variants of the invention or a pharmaceutical composition thereof.

The invention also provides pharmaceutical compositions comprising the polypeptide and protein variants disclosed herein and a pharmaceutically acceptable formulation agent. Such pharmaceutical compositions can be used in a method for treating a metabolic disorder, and the method comprises administering to a human patient in need thereof a pharmaceutical composition of the invention. Non-limiting examples of metabolic disorders that can be treated include type 1 and type 2 diabetes mellitus and obesity.

These and other aspects of the invention will be elucidated in the following detailed description of the invention.

DETAILED DESCRIPTION OF THE INVENTION

Figure 1:
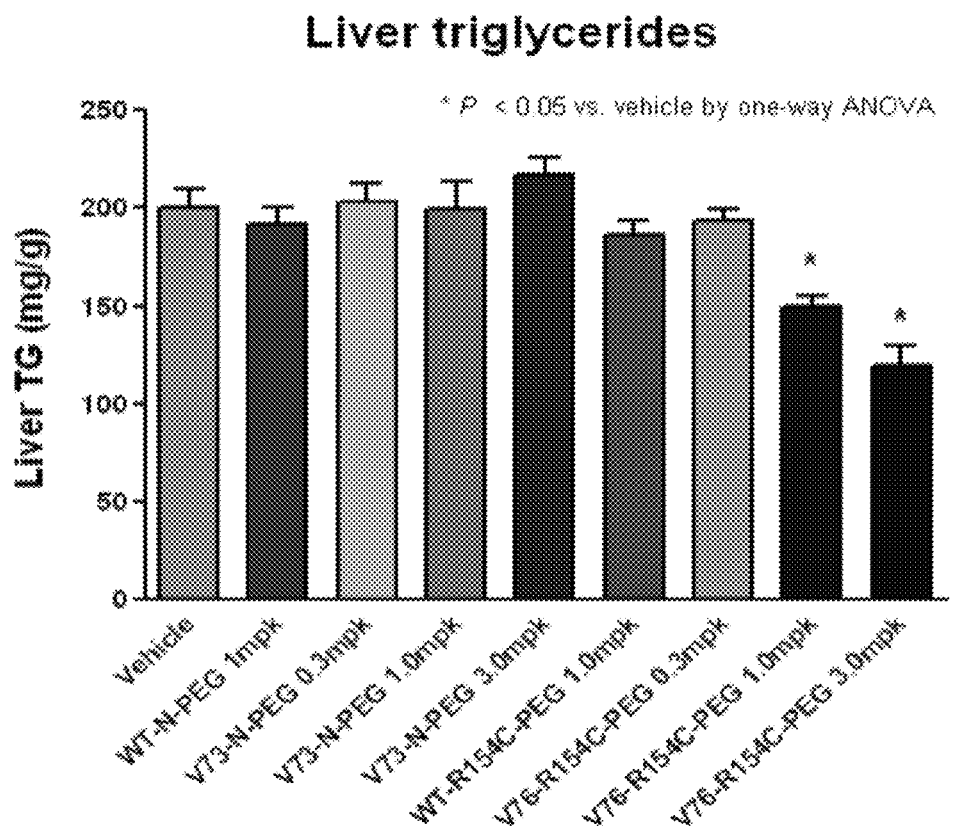
FIG. 1 is a graphical representation showing a drop in liver triglyceride levels following treatment of ob/ob mice for 12 days with PEGylated wild type FGF21 and the FGF21 variants of the invention. Liver samples (<50 mg) were homogenized in isopropanol:butylated hydroxytoluene (BHT or 2,6-di-tert-butyl-4-methylphenol) at a ratio of 1000:5, using Qiagen tissue lyser (with one 5-mm bead). Following homogenization, the samples were gently shaken for 45 min at room temperature and then spun down at 6000 rpm for 10 min at 4° C. The supernatants were collected and assayed for triglyceride content using the Wako triglyceride assay kit.

A significant challenge in the development of protein pharmaceuticals, such as FGF21, including the FGF21 protein variants of the present invention, is to cope with their physical and chemical instabilities. The compositional variety and characteristics of proteins define specific behaviors such as folding, conformational stability, and unfolding/denaturation. Such characteristics must be addressed to stabilize proteins when developing pharmaceutical formulation conditions utilizing aqueous protein solutions (Wang, W., Int. J. of Pharmaceutics, 18, (1999)). A desired effect of stabilizing therapeutic proteins of interest, e.g., the FGF21 protein variants of the present invention, is increasing resistance to proteolysis and enzymatic degradation, thereby improving protein stability and reducing protein aggregation.

Specifically, in pharmaceutical protein development, antimicrobial preservative agents such as phenol, m-cresol, methylparaben, resorcinol, and benzyl alcohol are necessary in parenteral pharmaceutical formulations that are intended to be a sterile, multi-use formulation. Unfortunately, these compounds often adversely affect the stability of the protein product, triggering association and aggregation, in particular (Maa et al., Int. J. of Pharmaceutics 140:155-168 (1996); Lam et al., Pharm. Res. 14(6):725-729 (1997)).

The FGF21 polypeptide and protein variants of the present invention represent modified versions of the full length, wild-type FGF21 polypeptide, as known in the art. FGF21 wild-type sequence will serve as a reference sequence (SEQ ID NO:1), for instance, when comparisons between the FGF21 wild-type sequence and the protein variants are necessary. The FGF21 wild-type sequence has NCBI reference sequence number NP_061986.1, and can be found in such issued patents as, e.g., U.S. Pat. No. 6,716,626B1, assigned to Chiron Corporation.

```
Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
```

```
                65                  70                  75                  80
Leu Gln Leu Lys Ala Leu Lys Pro Gly Val Ile Gln Ile Leu Gly Val
                    85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser
209
```

The corresponding cDNA sequence coding for the full-length FGF21 polypeptide (NCBI reference sequence number NM_019113.2) is shown below (SEQ ID NO:2)

```
  1 atggactcgg acgagaccgg gttcgagcac tcaggactgt gggtttctgt gctggctggt
 61 cttctgctgg gagcctgcca ggcacacccc atccctgact ccagtcctct cctgcaattc
121 gggggccaag tccggcagcg gtacctctac acagatgatg cccagcagac agaagcccac
181 ctggagatca gggaggatgg gacggtgggg ggcgctgctg accagagccc cgaaagtctc
241 ctgcagctga aagccttgaa gccgggagtt attcaaatct gggagtcaa gacatccagg
301 ttcctgtgcc agcggccaga tggggccctg tatggatcgc tccactttga ccctgaggcc
361 tgcagcttcc gggagctgct tcttgaggac ggatacaatg tttaccagtc gaagcccac
421 ggcctcccgc tgcacctgcc agggaacaag tccccacacc gggaccctgc accccgagga
481 ccagctcgct tcctgccact accaggcctg cccccccgcac tcccggagcc acccggaatc
541 ctggcccccc agccccccga tgtgggctcc tcggaccctc tgagcatggt gggaccttcc
601 cagggccgaa gcccagcta cgcttcctga
```

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art. A representative example of a mature FGF21 sequence has the following sequence (SEQ ID NO:3, which represents amino acid positions 29-209 of full length FGF21 protein sequence (NCBI reference sequence number NP_061986.1)):

```
His Pro Ile Pro Asp Ser Ser Pro Leu Leu Gln Phe Gly Gly Gln Val
                 5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80
```

```
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
            180
```

The corresponding cDNA sequence coding for the mature FGF21 polypeptide (SEQ ID NO:3) is shown below (SEQ ID NO:47):

```
  1 cacccatcc ctgactccag tcctctcctg caattcgggg gccaagtccg gcagcggtac
 61 ctctacacag atgatgccca gcagacagaa gcccacctgg agatcaggga ggatgggacg
121 gtggggggcg ctgctgacca gagccccgaa agtctcctgc agctgaaagc cttgaagccg
181 ggagttattc aaatcttggg agtcaagaca tccaggttcc tgtgccagcg gccagatggg
240 gccctgtatg gatcgctcca ctttgaccct gaggcctgca gcttccggga gctgcttctt
301 gaggacggat acaatgttta ccagtccgaa gcccacggcc tcccgctgca cctgccaggg
360 aacaagtccc cacaccggga ccctgcaccc cgaggaccag ctcgcttcct gccactacca
421 ggcctgcccc ccgcactccc ggagccaccc ggaatcctgg cccccccagcc ccccgatgtg
481 ggctcctcgg accctctgag catggtggga ccttcccagg gccgaagccc cagctacgct
541 tcctga
```

One skilled in the art of expression of proteins will recognize that methionine or methionine-arginine sequence can be introduced at the N-terminus of any of the FGF21 protein variants, for expression in *E. coli*, and are contemplated within the context of this invention.

The terms "FGF21 protein variant," "human FGF21 variant," "FGF21 polypeptide or protein variant," "variant," "FGF21 mutant," or any like terms, are defined as comprising human FGF21 in which a naturally occurring (i.e., wild-type) FGF21 amino acid sequence has been modified, e.g., in which at least one amino acid of the wild-type protein has been substituted by another amino acid, and/or removed. Additionally, the variants may include N- and/or C-terminal truncations relative to the wild-type FGF21 protein. Generally speaking, a variant possesses some modified property, structural or functional, of the wild-type protein. For example, the variant may have enhanced or improved physical stability in concentrated solutions (e.g., less hydrophobic mediated aggregation), enhanced or improved plasma stability when incubated with blood plasma or enhanced or improved bioactivity while maintaining a favorable bioactivity profile.

Acceptable amino acid substitutions and modifications which constitute differences between the FGF21 polypeptide and protein variants of the invention and wild-type FGF21 include, but are not limited to, one or more amino acid substitutions, including substitutions with non-naturally occurring amino acid analogs, and truncations. Thus, FGF21 protein variants include, but are not limited to, site-directed FGF21 mutants, truncated FGF21 polypeptides, proteolysis-resistant FGF21 mutants, aggregation-reducing FGF21 mutants, FGF21 combination mutants, and FGF21 fusion proteins, as described herein.

The variant may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. Accordingly, variants with enhanced pharmaceutical stability relative to wild-type FGF21, have improved physical stability in concentrated solutions under both physiological and preserved pharmaceutical formulation conditions, while maintaining biological potency. By way of non-limiting example, the variants of the invention may be more resistant to proteolysis and enzymatic degradation; may have improved stability; and may be less likely to aggregate, than their wild-type counterparts. As used herein, these terms are not mutually exclusive or limiting, it being entirely possible that a given variant has one or more modified properties of the wild-type protein.

The invention also encompasses a nucleic acid molecule encoding an FGF21 polypeptide or protein variant, or variant, comprising an amino acid sequence that is at least about 95% (alternately 96%, alternately 97%, alternately 98%, alternately 99%) identical to the amino acid sequence of SEQ ID NO:3, but wherein specific residues conferring a desirable property to the FGF21 protein variant, e.g., proteolysis-resistance, increased half life or aggregation-reducing properties and combinations thereof have not been further modified. In other words, with the exception of residues in the FGF21 mutant sequence that have been modified in order to confer proteolysis-resistance, aggregation-reducing, or other properties, about 5% (alternately 4%, alternately 3%, alternately 2%, alternately 1%) of all other amino acid residues in the FGF21 mutant sequence can be modified. Such FGF21 mutants possess at least one activity of the wild-type FGF21 polypeptide.

The invention also encompasses a nucleic acid molecule comprising a nucleotide sequence that is at least about 95% (alternately 96%, alternately 97%, alternately 98%, alternately 99%) identical to the nucleotide sequence of SEQ ID NO:47, but wherein the nucleotides encoding amino acid residues conferring the encoded FGF21 protein variant's proteolysis-resistance, aggregation-reducing or other properties have not been further modified. In other words, with the exception of nucleotides that encode residues in the FGF21 mutant sequence that have been modified in order to confer proteolysis-resistance, aggregation-reducing, or other properties, about 5% (alternately 4%, alternately 3%, alternately 2%, alternately 1%) of all other nucleotides in the FGF21 mutant sequence can be modified. Such nucleic acid molecules encode FGF21 mutant polypeptides possessing at least one activity of the wild-type FGF21 polypeptide.

Provided herein are methods used to generate the FGF21 polypeptides and protein variants of the invention, wherein such methods involve site-specific modification of the wild-type FGF21 protein, via e.g., truncations of the wild-type FGF21 protein, and the site-specific incorporation of amino acids at positions of interest within the wild-type FGF21 protein. Said modifications enhance the biological properties of the variants of the invention relative to the wild-type FGF21 protein, as well as, in some cases, serving as points of attachment for, e.g., labels and protein half-life extension agents, and for purposes of affixing said variants to the surface of a solid support. Related embodiments of the invention are methods of producing cells capable of producing said polypeptide and protein variants, and of producing vectors containing DNA encoding said variants.

In certain embodiments, such site-specific modifications are used to attach poly(ethylene glycol)(PEG) to proteins, polypeptides, and/or peptides. In other embodiments, such site-specific modifications are used to attach PEG-cholesterol conjugates (including micelles and liposomes) to proteins, polypeptides, and/or peptides. In other embodiments, such site-specific modifications are used to attach sugars (glycosylate) to proteins, polypeptides, and/or peptides.

In other embodiments, such site-specific modifications are used as means of attachment for the production of FGF21 wild-type and/or variant multimers, e.g., dimers (homodimers or heterodimers) or trimers. These multimeric FGF21 molecules may additionally have groups such as PEG, sugars, and/or PEG-cholesterol conjugates attached or be fused either amino-terminally or carboxy-terminally to other proteins such as Fc, HSA etc.

In other embodiments, such site-specific modifications are used to produce proteins, polypeptides and/or peptides wherein the position of the site-specifically incorporated pyrrolysine or pyrrolysine analogue allows for controlled orientation and attachment of such proteins, polypeptides and/or peptides onto a surface of a solid support or to have groups such as PEG, sugars and/or PEG-cholesterol conjugates attached.

In other embodiments, such site-specific modifications are used to site-specifically cross-link proteins, polypeptides and/or peptides thereby forming hetero-oligomers including, but not limited to, heterodimers and heterotrimers. In other embodiments, such site-specific modifications are used to site-specifically cross-link proteins, polypeptides and/or peptides thereby forming protein-protein conjugates, protein-polypeptide conjugates, protein-peptide conjugates, polypeptide-polypeptide conjugates, polypeptide-peptide conjugates or peptide-peptide conjugates.

Definitions

Various definitions are used throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "FGF21" refers to a member of the fibroblast growth factor (FGF) protein family. An amino acid sequence of FGF21 (GenBank Accession No. NP_061986.1) is set forth as SEQ ID NO:1, the corresponding polynucleotide sequence of which is set forth as SEQ ID NO:2 (NCBI reference sequence number NM_019113.2).

As used herein, the term "FGF21 receptor" refers to a receptor for FGF21 (Kharitonenkov, A, et al. (2008) Journal of Cellular Physiology 215:1-7; Kurosu, H, et al. (2007) JBC 282:26687-26695; Ogawa, Y, et al. (2007) PNAS 104:7432-7437).

The term "FGF21 polypeptide" refers to a naturally-occurring polypeptide expressed in humans. For purposes of this disclosure, the term "FGF21 polypeptide" can be used interchangeably to refer to any full-length FGF21 polypeptide, e.g., SEQ ID NO:1, which consists of 209 amino acid residues and which is encoded by the nucleotide sequence of SEQ ID NO:2; any mature form of the polypeptide, which consists of 181 amino acid residues, and in which the 28 amino acid residues at the amino-terminal end of the full-length FGF21 polypeptide (i.e., which constitute the signal peptide) have been removed, and variants thereof.

The term "isolated nucleic acid molecule" refers to a nucleic acid molecule of the present invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with its use in polypeptide production or its therapeutic, diagnostic, prophylactic or research use.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" when used in connection with biological materials such as nucleic acid molecules, polypeptides, host cells, and the like, refers to materials which are found in nature and are not manipulated by man. Similarly, "non-naturally occurring" as used herein refers to a material that is not found in nature or that has been structurally modified or synthesized by man. When used in connection with nucleotides, the term "naturally occurring" refers to the bases adenine (A), cytosine (C), guanine (G), thymine (T), and uracil (U). When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (PYL) and pyrroline-carboxy-lysine (PCL).

Pyrrolysine (PYL) is an amino acid naturally found within methylamine methyltransferases of methanogenic archaea of the family Methanosarcina. Pyrrolysine is a lysine analogue co-translationally incorporated at in-frame UAG codons in the respective mRNA, and it is considered the 22nd natural amino acid.

As described at least in PCT patent publication WO2010/48582 (applicant IRM, LLC), attempts to biosynthesize pyrrolysine (PYL) in E. coli resulted in the formation of a "demethylated pyrrolysine," referred to herein as pyrroline-carboxy-lysine, or PCL. "PCL," as used herein, refers to either PCL-A or PCL-B.

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) FGF21 protein sequence or the sequences of the FGF21 variants of the present invention. These include, but are not limited to, modified amino acids and/or amino acid analogues that are not one of the 20 naturally occurring amino acids, selenocysteine, pyrrolysine (PYL), or pyrroline-carboxy-lysine (PCL). Such non-natural amino acid residues can be introduced by substitution of naturally occurring amino acids, and/or by insertion of non-natural amino acids into the naturally occurring (wild-type) FGF21 protein sequence or the sequences of the FGF21 variants of the invention. The non-natural amino acid residue also can be incorporated such that a desired functionality is imparted to the FGF21 molecule, for example, the ability to link a functional moiety (e.g., PEG).

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem. Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

The term "amino acid mimetics," as used herein, refers to chemical compounds that have a structure that is different from the general chemical structure of an amino acid, but functions in a manner similar to a naturally occurring amino acid.

The term "biologically active FGF21 variant" refers to any FGF21 polypeptide variant described herein that possesses an activity of the wild-type FGF21 polypeptide, such as the ability to lower blood glucose, insulin, triglyceride, or cholesterol; reduce body weight; and to improve glucose tolerance, energy expenditure, or insulin sensitivity, regardless of the type or number of modifications that have been introduced into the FGF21 polypeptide variant. FGF21 polypeptide variants possessing a somewhat decreased level of FGF21 activity relative to the wild-type FGF21 polypeptide can nonetheless be considered to be biologically active FGF21 polypeptide variants.

The terms "effective amount" and "therapeutically effective amount" each refer to the amount of an FGF21 protein variant used to support an observable level of one or more biological activities of the wild-type FGF21 polypeptide, such as the ability to lower blood glucose, insulin, triglyceride or cholesterol levels; reduce liver triglyceride or lipid levels; reduce body weight; or improve glucose tolerance, energy expenditure, or insulin sensitivity. For example, a "therapeutically-effective amount" administered to a patient exhibiting, suffering, or prone to suffer from FGF21-associated disorders (such as type 1 or type 2 diabetes mellitus, obesity, or metabolic syndrome), is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human, but can also be an animal, more specifically, a companion animal (e.g., dogs, cats, and the like), farm animals (e.g., cows, sheep, pigs, horses, and the like) and laboratory animals (e.g., rats, mice, guinea pigs, and the like).

The term "pharmaceutically acceptable carrier" or "physiologically acceptable carrier" as used herein refers to one or more formulation materials suitable for accomplishing or enhancing the delivery of an FGF21 protein variant.

The term "antigen" refers to a molecule or a portion of a molecule that is capable of being bound by an antibody, and additionally that is capable of being used in an animal to produce antibodies that are capable of binding to an epitope of that antigen. An antigen may have one or more epitopes.

The term "native Fc" refers to molecule or sequence comprising the sequence of a non-antigen-binding fragment resulting from digestion of whole antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgA2). One example of a native Fc is a disulfide-bonded dimer resulting from papain digestion of an IgG (see Ellison et al., 1982, Nucleic Acids Res. 10: 4071-9). The term "native Fc" as used herein is generic to the monomeric, dimeric, and multimeric forms. The term "Fc variant" refers to a molecule or sequence that is modified from a native Fc but still comprises a binding site for the salvage receptor, FcRn (neonatal Fc receptor). International Publication Nos. WO 97/34631 and WO 96/32478 describe exemplary Fc variants, as well as interaction with the salvage receptor, and are hereby incorporated by reference. Thus, the term "Fc variant" can comprise a molecule or sequence that is humanized from a non-human native Fc. Furthermore, a native Fc comprises regions that can be removed because they provide structural features or biological activity that are not required for the fusion molecules of the FGF21 mutants of the present invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variants and sequences as defined above. As with Fc variants and native Fc molecules, the term "Fc domain" includes molecules in monomeric or multimeric form, whether digested from whole antibody or produced by other means. In some embodiments of the present invention, an Fc domain can be fused to FGF21 or a FGF21 mutant (including a truncated form of FGF21 or a FGF21 mutant) via, for example, a covalent bond between the Fc domain and the FGF21 sequence. Such fusion proteins can form multimers via the association of the Fc domains and both these fusion proteins and their multimers are an aspect of the present invention.

The term "polyethylene glycol" or "PEG" refers to a polyalkylene glycol compound or a derivative thereof, with or without coupling agents or derviatization with coupling or activating moieties.

The term "FGF21-associated disorders," and terms similarly used herein, includes but is not limited to obesity, type 1 and type 2 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders.

"Type 2 diabetes mellitus" is a condition characterized by excess glucose production in spite of the availability of insulin, and circulating glucose levels remain excessively high as a result of inadequate glucose clearance.

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin.

"Pancreatitis" is inflammation of the pancreas.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Nonalcoholic steatohepatitis (NASH)" is a liver disease, not associated with alcohol consumption, characterized by fatty change of hepatocytes, accompanied by intralobular inflammation and fibrosis.

"Glucose intolerance," or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity," in terms of the human subject, can be defined as that body weight over 20 percent above the ideal body weight for a given population (R. H. Williams, Textbook of Endocrinology, 1974, p. 904-916).

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Peripheral arterial disease" occurs when plaque builds up in the arteries that carry blood to the head, organs and limbs. Over time, plaque can harden and narrow the arteries which limits the flow of oxygen-rich blood to organs and other parts of the body.

"Atherosclerosis" is a vascular disease characterized by irregularly distributed lipid deposits in the intima of large and medium-sized arteries, causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body.

"Coronary heart disease", also called coronary artery disease, is a narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfuntion and problems with teeth and gums.

"Neuroapathies" are any diseases involving the cranial nerves or the peripheral or autonomic nervous system.

"Gastroparesis" is weakness of gastric peristalsis, which results in delayed emptying of the bowels.

The critically ill patients encompassed by the present invention generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

As used herein, the singular forms "a," "an" and "the" include plural references unless the content clearly dictates otherwise. Thus, for example, reference to "an antibody" includes a mixture of two or more such antibodies.

As used herein, the term "about" refers to +/−20%, +/−10%, or +/−5% of a value.

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "individual", "subject", "host" and "patient" are used interchangeably and refer to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

As used herein, the term "biological molecule" includes, but is not limited to, polypeptides, nucleic acids, and saccharides.

As used herein, the term "modulating" refers to a change in the quality or quantity of a gene, protein, or any molecule that is inside, outside, or on the surface of a cell. The change can be an increase or decrease in expression or level of the molecule. The term "modulates" also includes changing the quality or quantity of a biological function/activity including, without limitation, the ability to lower blood glucose, insulin, triglyceride, or cholesterol levels; to reduce liver lipid or liver triglyceride levels; to reduce body weight; and to improve glucose tolerance, energy expenditure, or insulin sensitivity.

As used herein, the term "modulator" refers to a composition that modulates one or more physiological or biochemical events associated with an FGF21-associated disorder, such as type 1 or type 2 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In some embodiments, if the gene product is proteinaceous, it exhibits a biological activity. In some embodiments, if the gene product is a nucleic acid, it can be translated into a proteinaceous gene product that exhibits a biological activity.

"Modulation of FGF21 activity," as used herein, refers to an increase or decrease in FGF21 activity that can be a result of, for example, interaction of an agent with an FGF21 polynucleotide or polypeptide, inhibition of FGF21 transcription and/or translation (e.g., through antisense or siRNA interaction with the FGF21 gene or FGF21 transcript, through modulation of transcription factors that facilitate FGF21 expression), and the like. For example, modulation of a biological activity refers to an increase or a decrease in a biological activity. FGF21 activity can be assessed by means including, without limitation, assaying blood glucose, insulin, triglyceride, or cholesterol levels in a subject, assessing FGF21 polypeptide levels, or by assessing FGF21 transcription levels. Comparisons of FGF21 activity can also be accomplished by, e.g., measuring levels of an FGF21 downstream biomarker, and measuring increases in FGF21 signaling. FGF21 activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and an FGF21 receptor; or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

A "FGF21 downstream biomarker," as used herein, is a gene or gene product, or measurable indicia of a gene or gene product. In some embodiments, a gene or activity that is a downstream marker of FGF21 exhibits an altered level of expression, or in a vascular tissue. In some embodiments, an activity of the downstream marker is altered in the presence of an FGF21 modulator. In some embodiments, the downstream markers exhibit altered levels of expression when FGF21 is perturbed with an FGF21 modulator of the present invention. FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, in the context of the present invention, FGF21 modulators may increase the activity of an FGF21 receptor. In one embodiment, one or both of FGFR-1c or FGFR-4 may be upregulated in response to an FGF21 modulator. Upregulation can also refer to an FGF21-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21 receptor; or to increase an FGF21 downstream marker. The FGFR21 receptor can be one or both of FGFR-1c or FGFR-4. Up-regulation may be at least 25%, at least 50%, at least 75%, at least 100%, at least 150%, at least 200%, at least 250%, at least 400%, or at least 500% as compared to a control.

As used herein, the term "N-terminus" refers to at least the first 10 amino acids of a protein.

As used herein, the terms "N-terminal domain" and "N-terminal region" are used interchangeably and refer to a fragment of a protein that begins at the first amino acid of the protein and ends at any amino acid in the N-terminal half of the protein. For example, the N-terminal domain of FGF21 is from amino acid 1 of SEQ ID NO:1 to any amino acid between about amino acids 10 and 105 of SEQ ID NO:1.

As used herein, the term "C-terminus" refers to at least the last 10 amino acids of a protein.

As used herein, the terms "C-terminal domain" and "C-terminal region" are used interchangeably and refer to a fragment of a protein that begins at any amino acid in the C-terminal half of the protein and ends at the last amino acid of the protein. For example, the C-terminal domain of FGF21 begins at any amino acid from amino acid 105 to about amino acid 200 of SEQ ID NO:1 and ends at amino acid 209 of SEQ ID NO:1.

The term "domain" as used herein refers to a structural part of a biomolecule that contributes to a known or suspected function of the biomolecule. Domains may be co-extensive with regions or portions thereof and may also incorporate a portion of a biomolecule that is distinct from a particular region, in addition to all or part of that region.

As used herein, the term "signal domain" (also called "signal sequence" or "signal peptide") refers to a peptide domain that resides in a continuous stretch of amino acid sequence at the N-terminal region of a precursor protein (often a membrane-bound or secreted protein) and is involved in post-translational protein transport. In many cases the signal domain is removed from the full-length protein by specialized signal peptidases after the sorting process has been completed. Each signal domain specifies a particular destination in the cell for the precursor protein. The signal domain of FGF21 is amino acids 1-28 of SEQ ID NO:1.

As used herein, the term "receptor binding domain" refers to any portion or region of a protein that contacts a membrane-bound receptor protein, resulting in a cellular response, such as a signaling event.

As used herein, the term "ligand binding domain" refers to any portion or region of a protein retaining at least one qualitative binding activity of a corresponding native sequence of FGF21.

The term "region" refers to a physically contiguous portion of the primary structure of a biomolecule. In the case of proteins, a region is defined by a contiguous portion of the amino acid sequence of that protein. In some embodiments a "region" is associated with a function of the biomolecule.

The term "fragment" as used herein refers to a physically contiguous portion of the primary structure of a biomolecule. In the case of proteins, a portion is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of oligonucleotides, a portion is defined by a contiguous portion of the nucleic acid sequence of that oligonucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, portions of biomolecules have a biological activity. In the context of the present invention, FGF21 polypeptide fragments do not comprise the entire FGF21 polypeptide sequence set forth in SEQ ID NO:1.

A "native sequence" polypeptide is one that has the same amino acid sequence as a polypeptide derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

As used herein, the phrase "homologous nucleotide sequence," or "homologous amino acid sequence," or variations thereof, refers to sequences characterized by a homology, at the nucleotide level or amino acid level, of at least a specified percentage and is used interchangeably with "sequence identity". Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity. In some embodiments, a nucleotide or amino acid sequence is homologous if it has at least 60%, 70%, 80%, 85%, 90%, 95%, 96%, 97%, 98%, or 99% identity. In some embodiments, a nucleotide or amino acid sequence is homologous if it has 1-10, 10-20, 20-30, 30-40, 40-50, or 50-60 nucleotide/amino acid substitutions, additions, or deletions. In some embodiments, the homologous amino acid sequences have no more than 5 or no more than 3 conservative amino acid substitutes.

Percent homology or identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, homology between the probe and target is between about 75% to about 85%. In some embodiments, nucleic acids have nucleotides that are at least about 95%, about 97%, about 98%, about 99% and about 100% homologous to SEQ ID NO:2, or a portion thereof.

Homology may also be at the polypeptide level. In some embodiments, polypeptides are about 95%, about 97%, about 98%, about 99% and about 100% homologous to SEQ ID NO:1, or a portion thereof. The degree or percentage identity of an FGF21 variant of the present invention ("invention sequence" e.g. Variant 1 or SEQ ID NO:5) and a different amino acid sequence ("foreign sequence" e.g. SEQ ID NO:1 with L174 changed to P174) is calculated as the number of exact matches in an alignment of the two sequences divided by the length of the "invention sequence" or the "foreign sequence", whichever is shortest. The result is expressed as percent identity. For example, Variant 1 (SEQ ID NO:5), has 94.9% identity to wild type FGF21 with L174 changed to P174 (SEQ ID NO:1 with L174 changed to P174). For these two sequences there are 168 identical amino acids and the total length is 177 amino acids. Thus, the percent identity is (168/177)×100=94.9%.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Naturally occurring disulfide bonds, as provided by cysteine residues, generally increase thermodynamic stability of proteins. Successful examples of increased thermodynamic stability, as measured in increase of the melting temperature, are multiple disulfide-bonded mutants of the enzymes T4 lysozyme (Matsumura, et al., PNAS 86:6562-6566 (1989)) and barnase (Johnson et al., J. Mol. Biol. 268:198-208 (1997)). An aspect of the present invention is an enhancement of the physical stability of FGF21 in the presence of a preservative, achieved by the presence of disulfide bonds within the variants, which constrain the flexibility of wild type FGF21 and thereby limit access of the preservative to the hydrophobic core of the protein.

The second aspect of the present invention therefore provides variants of human FGF21, or a biologically active peptide thereof, with enhanced pharmaceutical stability engendered by the incorporation of additional disulfide bonds, e.g., via incorporating or substituting cysteine residues into the wild-type FGF21 protein or the polypeptide and protein variants of the invention. One skilled in the art will recognize that the native cysteines, cysteine 103 and cysteine 121, could be utilized as loci to introduce a novel disulfide bond that may impart improved properties, in addition to the suggested embodiments describer herein.

These include FGF-21 with the substitution of a cysteine for two or more of the following: glutamine 46, arginine 47, tyrosine 48, leucine 49, tyrosine 50, threonine 51, aspartate 52, aspartate 53, alanine 54, glutamine 55, glutamine 56, threonine 57, glutamate 58, alanine 59, histidine 60, leucine 61, glutamate 62, isoleucine 63, valine 69, glycine 70, glycine 71, alanine 72, alanine 73, leucine 144, histidine 145, leucine 146, proline 147, glycine 148, asparagine 149, lysine 150, serine 151, proline 152, histidine 153, arginine 154, aspartate 155, proline 156, alanine 157, proline 158, arginine 159, glycine 160, proline 161, alanine 162, arginine 163. phenylalanine 164, wherein the numbering of the amino acids is based on the full length 209 amino acid hFGF21 sequence SEQ ID NO:1

Furthermore, variants of human FGF21, or a biologically active peptide thereof, are provided with engineered disulfide bonds, in addition to the naturally occurring one at Cys103-Cys121, are as follows: Gln46Cys-Ala59Cys, Gln46Cys-His60Cys, Gln46Cys-Leu61Cys, Gln46Cys-Glu62Cys, Gln46Cys-Ile63Cys, Arg47Cys-Ala59Cys, Arg47Cys-His60Cys, Arg47Cys-Leu61Cys, Arg47Cys-Glu62Cys, Arg47Cys-Ile63Cys, Tyr48Cys-Ala59Cys, Tyr48Cys-His60Cys, Tyr48Cys-Leu61Cys, Tyr48Cys-Glu62Cys, Tyr48Cys-Ile63Cys, Leu49Cys-Ala59Cys, Leu49Cys-His60Cys, Leu49Cys-Leu61Cys, Leu49Cys-Glu62Cys, Leu49Cys-Ile63Cys, Tyr50Cys-Ala59Cys, Tyr50Cys-His60Cys, Tyr50Cys-Lue61Cys, Tyr50Cys-Glu62Cys, Tyr50Cys-Ile63Cys, Leu144Cys-Gly160Cys, Leu144Cys-Pro161Cys, Leu144Cys-Ala162Cys, Leu144Cys-Arg163Cys, Leu144Cys-Phe164Cys, His145Cys-Gly160Cys, His145Cys-Pro161Cys, His145Cys-Ala162Cys, His145Cys-Arg163Cys, His145Cys-Phe164Cys, Leu146Cys-Gly160Cys, Leu146Cys-Pro161Cys, Leu146Cys-Ala162Cys, Leu146Cys-Arg163Cys, Leu146Cys-Phe164Cys, Pro147Cys-Gly160Cys, Pro147Cys-Pro161Cys, Pro147Cys-Ala162Cys, Pro147Cys-Arg163Cys, Pro147Cys-Phe164Cys, Gly148Cys-Gly160Cys, Gly148Cys-Pro161Cys, Gly148Cys-Ala162Cys, Gly148Cys-Arg163Cys, Gly148Cys-Phe164Cys, Thr57Cys-Val69Cys, Thr57Cys-Gly70Cys, Thr57Cys-Gly71Cys, Thr57Cys-Ala72Cys, Thr57Cys-Ala73Cys, Glu58Cys-Val69Cys, Glu58Cys-Glu70Cys, Glu58Cys-G71Cys, Glu58Cys-Ala72Cys, Glu58Cys-Ala73Cys, Ala59Cys-Val69Cys, Ala59Cys-Gly70Cys, Ala59Cys-Gly71Cys, Ala59Cys-Ala72Cys, Ala59Cys-Ala73Cys, His60Cys-Val69Cys, His60Cys-Gly70Cys, His60Cys-Gly71Cys, His60Cys-Ala72Cys, His60Cys-Ala73Cys, Leu61Cys-Val69Cys, Leu61Cys-Gly70Cys, Leu61Cys-Gly71Cys, Leu61Cys-Ala72Cys, Leu61Cys-Ala73Cys, Arg47Cys-Gly148Cys, Tyr48Cys-Gly148Cys, Leu49Cys-Gly148Cys, Tyr50Cys-Gly148Cys, Thr51Cys-Gly148Cys, Asp52Cys-Gly148Cys, Asp53Cys-Gly148Cys, Ala54Cys-Gly148Cys, Gln55Cys-Gly148Cys, Gln56Cys-Gly148Cys, Thr57Cys-Gly148Cys, Glu58Cys-Gly148Cys, Arg47Cys-Asn149Cys, Tyr48Cys-Asn149Cys, Leu49Cys-Asn149Cys, Tyr50Cys-Asn149Cys, Thr51Cys-Asn149Cys, Asp52Cys-Asn149Cys, Asp53Cys-Asn149Cys, Ala54Cys-Asn149Cys, Gln55Cys-Asn149Cys, Gln56Cys-Asn149Cys, Thr57Cys-Asn149Cys, Glu58Cys-Asn149Cys, Arg47Cys-Lys150Cys, Tyr48Cys-Lys150Cys, Leu49Cys-Lys150Cys, Tyr50Cys-Lys150Cys, Thr51Cys-Lys150Cys, Asp52Cys-Lys150Cys, Asp53Cys-Lys150Cys, Ala54Cys-Lys150Cys, Gln55Cys-Lys150Cys, Gln56Cys-Lys150Cys, Thr57Cys-Lys150Cys, Glu58Cys-Lys150Cys, Arg47Cys-Ser151Cys, Tyr48Cys-Ser151Cys, Leu49Cys-Ser151Cys, Tyr50Cys-Ser151Cys, Thr51Cys-Ser151Cys, Asp52Cys-Ser151Cys, Asp53Cys-Ser151Cys, Ala54Cys-Ser151Cys, Gln55Cys-Ser151Cys, Gln56Cys-Ser151Cys, Thr57Cys-Ser151Cys, Glu58Cys-Ser151Cys, Arg47Cys-Pro152Cys, Tyr48Cys-Pro152Cys, Leu49Cys-Pro152Cys, Tyr50Cys-Pro152Cys, Thr51Cys-Pro152Cys, Asp52Cys-Pro152Cys, Asp53Cys-Pro152Cys, Ala54Cys-Pro152Cys, Gln55Cys-Pro152Cys, Gln56Cys-Pro152Cys, Thr57Cys-Pro152Cys, Glu58Cys-Pro152Cys, Arg47Cys-His153Cys, Tyr48Cys-His153Cys, Leu49Cys-His153Cys, Tyr50Cys-His153Cys, Thr51Cys-His153Cys, Asp52Cys-His153Cys, Asp53Cys-His153Cys, Ala54Cys-His153Cys, Gln55Cys-His153Cys, Gln56Cys-His153Cys, Thr57Cys-His153Cys, Glu58Cys-His153Cys, Arg47Cys-Arg154Cys, Tyr48Cys-Arg154Cys, Leu49Cys-Arg154Cys, Tyr50Cys-Arg154Cys, Thr51Cys-Arg154Cys, Asp52Cys-Arg154Cys, Asp53Cys-Arg154Cys, Ala54Cys-Arg154Cys, Gln55Cys-Arg154Cys, Gln56Cys-Arg154Cys, Thr57Cys-Arg154Cys, Glu58Cys-Arg154Cys, Arg47Cys-Asp155Cys, Tyr48Cys-Asp155Cys, Leu49Cys-Asp155Cys, Tyr50Cys-Asp155Cys, Thr51Cys-Asp155Cys, Asp52Cys-Asp155Cys, Asp53Cys-Asp155Cys, Ala54Cys-Asp155Cys, Gln55Cys-Asp155Cys, Gln56Cys-Asp155Cys, Thr57Cys-Asp155Cys, Glu58Cys-Asp155Cys, Arg47Cys-Pro156Cys, Tyr48Cys-Pro156Cys, Leu49Cys-Pro156Cys, Tyr50Cys-Pro156Cys, Thr51Cys-Pro156Cys, Asp52Cys-Pro156Cys, Asp53Cys-Pro156Cys, Ala54Cys-Pro156Cys, Gln55Cys-Pro156Cys, Gln56Cys-Pro156Cys, Thr57Cys-Pro156Cys, Glu58Cys-Pro156Cys, Arg47Cys-Ala157Cys, Tyr48Cys-Ala157Cys, Leu49Cys-Ala157Cys, Tyr50Cys-Ala157Cys, Thr51Cys-Ala157Cys, Asp52Cys-Ala157Cys, Asp53Cys-Ala157Cys, Ala54Cys-Ala157Cys, Gln55Cys-Ala157Cys, Gln56Cys-Ala157Cys, Thr57Cys-Ala157Cys, Glu58Cys-Ala157Cys, Arg47Cys-Pro158Cys, Tyr48Cys-Pro158Cys, Leu49Cys-Pro158Cys, Tyr50Cys-Pro158Cys, Thr51Cys-Pro158Cys, Asp52Cys-Pro158Cys, Asp53Cys-Pro158Cys, Ala54Cys-Pro158Cys, Gln55Cys-Pro158Cys, Gln56Cys-Pro158Cys, Thr57Cys-Pro158Cys, Glu58Cys-Pro158Cys, Arg47Cys-Arg159Cys, Tyr48Cys-Arg159Cys, Leu49Cys-Arg159Cys, Tyr50Cys-Arg159Cys, Thr51Cys-Arg159Cys, Asp52Cys-Arg159Cys, Asp53Cys-Arg159Cys, Ala54Cys-Arg159Cys, Gln55Cys-Arg159Cys, Gln56Cys-Arg159Cys, Thr57Cys-Arg159Cys, Glu58Cys-Arg159Cys, Arg47Cys-G160Cys, Tyr48Cys-G160Cys, Leu49Cys-G160Cys, Tyr50Cys-Gly160Cys, Thr51Cys-Gly160Cys, Asp52Cys-Gly160Cys, Asp53Cys-Gly160Cys, Ala54Cys-Gly160Cys, Gln55Cys-Gly160Cys, Gln56Cys-Gly160Cys, Thr57Cys-Gly160Cys, Glu58Cys-Gly160Cys, Arg47Cys-Pro161Cys, Tyr48Cys-Pro161Cys, Leu49Cys-Pro161 Cys, Tyr50Cys-Pro161 Cys, Thr51Cys-Pro161Cys, Asp52Cys-Pro161 Cys, Asp53Cys-Pro161 Cys, Ala54Cys-Pro161 Cys, Gln55Cys-Pro161Cys, Gln56Cys-Pro161Cys, Thr57Cys-Pro161Cys, Glu58Cys-Pro161Cys, Arg47Cys-Ala162Cys, Tyr48Cys-Ala162Cys, Leu49Cys-Ala162Cys, Tyr50Cys-Ala162Cys, Thr51Cys-Ala162Cys, Asp52Cys-Ala162Cys, Asp53Cys-Ala162Cys, Ala54Cys-Ala162Cys, Gln55Cys-Ala162Cys, Gln56Cys-Ala162Cys, Thr57Cys-Ala162Cys, Glu58Cys-Ala162Cys, Arg47Cys-Arg163Cys, Tyr48Cys-Arg163Cys, Leu49Cys-Arg163Cys, Tyr50Cys-Arg163Cys, Thr51Cys-Arg163Cys, Asp52Cys-Arg163Cys, Asp53Cys-Arg163Cys, Ala54Cys-Arg163Cys, Gln55Cys-Arg163Cys, Gln56Cys-Arg163Cys, Thr57Cys-Arg163Cys, Glu58Cys-Arg163Cys The third aspect of the present invention provides variants of human FGF21, or a biologically active peptide thereof, comprising a substitution of any charged and/or polar but uncharged amino acid at any of the amino acid positions indicated in the first embodiment of the present invention combined with the substitution of a cysteine at two or more amino acid positions indicated in the second embodiment of the invention.

It is well known in the art that a significant challenge in the development of protein pharmaceuticals is to deal with the physical and chemical instabilities of proteins. This is even more apparent when a protein pharmaceutical formulation is intended to be a multiple use, injectable formulation requiring a stable, concentrated and preserved solution, while maintaining a favorable bioactivity profile. Detailed biophysical characterization of wild-type FGF21 established that a concentrated protein solution (>5 mg/ml), when exposed to stress conditions, such as high temperature or low pH, lead to accelerated association and aggregation (i.e., poor physical stability and biopharmaceutical properties). Exposure of a concentrated protein solution of FGF21 to pharmaceutical preservatives (e.g., m-cresol) also had a negative impact on physical stability.

Therefore, an embodiment of the present invention is to enhance physical stability of concentrated solutions, while maintaining chemical stability and biological potency, under both physiological and preserved formulation conditions. It is thought that association and aggregation may result from hydrophobic interactions, since, at a given protein concentration, temperature, and ionic strength have considerable impact on physical stability. For the most part, non-conserved, presumed surface exposed amino acid residues were targeted. The local environment of these residues was analyzed and, those that were not deemed structurally important were selected for mutagenesis. One method to initiate specific changes is to further decrease the pI of the protein by introducing glutamic acid residues ("glutamic acid scan"). It is hypothesized that the introduction of charged substitutes would inhibit hydrophobic-mediated aggregation via charge-charge repulsion and potentially improve preservative compatibility. In addition, one skilled in the art would also recognize that with sufficient degree of mutagenesis the pI could be shifted into a basic pH range by the introduction of positive charge with or without concomitant decrease in negative charge, thus allowing for charge-charge repulsion.

Although the embodiments of the present invention concern the physical and chemical stability under both physiological and preserved pharmaceutical formulation conditions, maintaining the biological potency of the variants as compared to wild-type FGF21 is an important factor of consideration as well. Therefore, the biological potency of the variants of the present invention is defined by the ability of the variants to affect glucose uptake as measured in the in vitro 3T3-L1 adipocyte 2-DOG uptake cell assay (Example 3) and/or the lowering of plasma glucose levels, as well as, plasma triglycerides, as measured in vivo in the ob/ob mouse assay (Example 5).

The variants of FGF21 administered according to this invention may be generated and/or isolated by any means known in the art. The most preferred method for producing the variant is through recombinant DNA methodologies and is well known to those skilled in the art. Such methods are described in Current Protocols in Molecular Biology (John Wiley & Sons, Inc.), which is incorporated herein by reference.

Additionally, the preferred embodiments include a biologically active peptide derived from the variant described herein. Such a peptide will contain at least one of the substitutions described and the variant will possess biological activity. The peptide may be produced by any and all means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., Proc. Natl. Acad. Sci. (USA) 85:2324-2328 (1988), and J. Cell. Phys. Suppl. 5:101-106 (1987). Therefore, the selection of fragments or peptides of the variant is based on criteria known in the art. For example, it is known that dipeptidyl peptidase IV (DPP-IV) is a serine type protease involved in inactivation of neuropeptides, endocrine peptides, and cytokines (Damme et al. Chem. Immunol. 72: 42-56, (1999)). The N-terminus of FGF21 (HisProIlePro) contains two dipeptides that could potentially be substrates to DPP-IV, resulting in a fragment of FGF21 truncated at the N-terminus by 4 amino acids. Unexpectedly, this fragment of wild-type FGF21 has been demonstrated to retain biological activity (Table 2), thus, variants of the present invention truncated at the N-terminus by up to 4 amino acids, is an embodiment of the present invention.

The invention also encompasses polynucleotides encoding the above-described variants that may be in the form of RNA or in the form of DNA, which DNA includes cDNA, genomic DNA, and synthetic DNA. The DNA may be double-stranded or single-stranded. The coding sequences that encode the variants of the present invention may vary as a result of the redundancy or degeneracy of the genetic code.

The polynucleotides that encode for the variants of the invention may include the following: only the coding sequence for the variant, the coding sequence for the variant and additional coding sequence such as a functional polypeptide, or a leader or secretory sequence or a pro-protein sequence; the coding sequence for the variant and non-coding sequence, such as introns or non-coding sequence 5' and/or 3' of the coding sequence for the variant. Thus the term "polynucleotide encoding a variant" encompasses a polynucleotide that may include not only coding sequence for the variant but also a polynucleotide, which includes additional coding and/or non-coding sequence.

The invention further relates to variants of the described polynucleotides that encode for fragments, analogs and derivatives of the polypeptide that contain the indicated substitutions. The variant of the polynucleotide may be a naturally occurring allelic variant of the human FGF21 sequence, a non-naturally occurring variant, or a truncated variant as described above. Thus, the present invention also includes polynucleotides encoding the variants described above, as well as variants of such polynucleotides, which variants encode for a fragment, derivative or analog of the disclosed variant. Such nucleotide variants include deletion variants, substitution variants, truncated variants, and addition or insertion variants as long as at least one of the indicated amino acid substitutions of the first or second embodiments is present.

The polynucleotides of the invention will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. The FGF21 variant can be expressed in mammalian cells, insect, yeast, bacterial or other cells under the control of appropriate promoters. Cell free translation systems can also be employed to produce such proteins using RNAs derived from DNA constructs of the present invention.

*E. coli* is a prokaryotic host useful particularly for cloning the polynucleotides of the present invention. Other microbial hosts suitable for use include *Bacillus subtilus, Salmonella typhimurium*, and various species of *Serratia, Pseudomonas, Streptococcus*, and *Staphylococcus*, although others may also be employed as a matter of choice. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phages lambda or T7. The promoters will typically control expression, optionally with an operator sequence, and have ribosome binding site sequences and the like, for initiating and completing transcription and translation.

One skilled in the art of expression of proteins will recognize that methionine or methionine-arginine sequence can be introduced at the N-terminus of the mature sequence (SEQ ID NO: 3) for expression in *E. coli* and are contemplated within the context of this invention. Thus, unless otherwise noted, variants of the present invention expressed in *E. coli* have a methionine sequence introduced at the N-terminus.

Other microbes, such as yeast or fungi, may also be used for expression. *Pichia pastoris, Saccharomyces cerevisiae, Schizosaccharomyces pombe,* and *Pichia angusta* are examples of preferred yeast hosts, with suitable vectors having expression control sequences, such as promoters, including 3-phosphoglycerate kinase or other glycolytic enzymes, and an origin of replication, termination sequences and the like as desired. *Aspergillus niger, Trichoderma reesei;* and *Schizophyllum commune,* are examples of fungi hosts, although others may also be employed as a matter of choice.

Mammalian tissue cell culture may also be used to express and produce the polypeptides of the present invention. Eukaryotic cells are actually preferred, because a number of suitable host cell lines capable of secreting intact variants have been developed in the art, and include the CHO cell lines, various COS cell lines, NSO cells, Syrian Hamster Ovary cell lines, HeLa cells, or human embryonic kidney cell lines (i.e. HEK293, HEK293EBNA).

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from SV40, adenovirus, bovine papilloma virus, cytomegalovirus, Raus sarcoma virus, and the like. Preferred polyadenylation sites include sequences derived from SV40 and bovine growth hormone.

The vectors containing the polynucleotide sequences of interest (e.g., the variants of FGF21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, Methods in Enzymology 182: 83-9 (1990) and Scopes, Protein Purification: Principles and Practice, Springer-Verlag, NY (1982). The purification step(s) selected will depend, for example, on the nature of the production process used for the variants of FGF21.

The FGF21 variant-containing compositions should be formulated and dosed in a fashion consistent with good medical practice, taking into account the clinical condition of the patient, the site of delivery of the FGF21 variant composition, the method of administration, the scheduling of administration, and other factors known to practitioners. The "therapeutically effective amount" of the FGF21 variant for purposes herein is thus determined by such considerations.

The pharmaceutical compositions of the FGF21 variants and of the present invention may be administered by any means that achieve the generally intended purpose: to treat type 1 and type 2 diabetes mellitus, obesity, metabolic syndrome, or critically ill patients. The term "parenteral" as used herein refers to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein an FGF21 variant is present in an amount that is effective to achieve the desired medical effect for treatment type 1 or type 2 diabetes mellitus, obesity, or metabolic syndrome. While individual needs may vary from one patient to another, the determination of the optimal ranges of effective amounts of all of the components is within the ability of the clinician of ordinary skill.

The variants of FGF21 of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [Remington's Pharmaceutical Sciences 16th edition (1980)]. The variants of the present invention may be combined with a pharmaceutically acceptable buffer, and the pH adjusted to provide acceptable stability, and a pH acceptable for administration.

For parenteral administration, in one embodiment, the FGF21 variants are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF21 variant, as determined by good medical practice and the clinical condition of the individual patient. A typical dose range for the FGF21 variants of the present invention will range from about 0.01 mg per day to about 1000 mg per day (or about 0.05 mg per week to about 5000 mg per week administered once per week) for an adult. Preferably, the dosage ranges from about 0.1 mg per day to about 100 mg per day (or about 0.5 mg per week to about 500 mg per week adminsered once per week), more preferably from about 1.0 mg/day to about 10 mg/day (or about 5 mg per week to about 50 mg per week administered once per week). Most preferably, the dosage is about 1-5 mg/day (or about 5 mg per week to about 25 mg per week administered once per week). The appropriate dose of an FGF21 variant administered will result in lowering blood glucose levels and increasing energy expenditure by faster and more efficient glucose utilization, and thus is useful for treating type 1 and type 2 diabetes mellitus, obesity and metabolic syndrome.

In addition, because hyperglycemia and insulin resistance are common in critically ill patients given nutritional support, some ICUs administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe, et al. N Engl J. Med., 345(19):1359, (2001)). Thus, variants of FGF21 of the present invention are uniquely suited to help restore metabolic stability in metabolically unstable critically ill patients. Variants of FGF21 are unique in that they stimulate glucose uptake and enhances insulin sensitivity but do not induce hypoglycemia.

In another aspect of the present invention, variants of FGF21 for use as a medicament for the treatment of type 1 and type 2 diabetes mellitus, obesity, metabolic syndrome, or critically ill patients is contemplated.

Having now described the present invention in detail, the same will be more clearly understood by reference to the following examples, which are included herewith for purposes of illustration only and are not intended to be limiting of the invention.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); and Sambrook et al., Molecular Cloning: A Laboratory Manual (2nd Edition, 1989).

Site-Specific FGF21 Mutants

The term "site-specific FGF21 mutant" or "substituted FGF21 mutant" refers to an FGF21 mutant polypeptide having an amino acid sequence that differs from the amino acid sequence of a naturally occurring FGF21 polypeptide sequence, e.g., SEQ ID NO:1 and variants thereof. Site-specific FGF21 mutants can be generated by introducing amino acid substitutions, either conservative or non-conservative and using naturally or non-naturally occurring amino acids, at particular positions of the FGF21 polypeptide.

"Conservative amino acid substitution" can involve a substitution of a native amino acid residue (i.e., a residue found in a given position of the wild-type FGF21 polypeptide sequence) with a normative residue (i.e., a residue that is not found in a given position of the wild-type FGF21 polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:
(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, H is, Lys, Arg;
(5) residues that influence chain orientation: Gly, Pro;
(6) aromatic: Trp, Tyr, Phe; and
(7) selenocysteine, pyrrolysine (PYL), and pyrroline-carboxy-lysine (PCL).

Conservative substitutions can involve the exchange of a member of one of these classes for another member of the same class. Non-conservative substitutions can involve the exchange of a member of one of these classes for a member from another class.

Desired amino acid substitutions (whether conservative or non-conservative) can be determined by those skilled in the art at the time such substitutions are desired.

Truncated FGF21 Polypeptides

One embodiment of the present invention is directed to truncated forms of the mature FGF21 polypeptide (SEQ ID NO:3). This embodiment of the present invention arose from an effort to identify truncated FGF21 polypeptides that are capable of providing an activity that is similar, and in some instances superior, to untruncated forms of the mature FGF21 polypeptide.

As used herein, the term "truncated FGF21 polypeptide" refers to an FGF21 polypeptide in which amino acid residues have been removed from the amino-terminal (or N-terminal) end of the FGF21 polypeptide, amino acid residues have been removed from the carboxyl-terminal (or C-terminal) end of the FGF21 polypeptide, or amino acid residues have been removed from both the amino-terminal and carboxyl-terminal ends of the FGF21 polypeptide. The various truncations disclosed herein were prepared as described herein.

The activity of N-terminally truncated FGF21 polypeptides and C-terminally truncated FGF21 polypeptides can be assayed using an in vitro phospho-ERK assay. Specific details of the in vitro assays that can be used to examine the activity of truncated FGF21 polypeptides can be found in the examples.

The activity of the truncated FGF21 polypeptides of the present invention can also be assessed in an in vivo assay, such as ob/ob mice. Generally, to assess the in vivo activity of a truncated FGF21 polypeptide, the truncated FGF21 polypeptide can be administered to a test animal intraperitoneally. After a desired incubation period (e.g., one hour or more), a blood sample can be drawn, and blood glucose levels can be measured.

a. N-Terminal Truncations

In some embodiments of the present invention, N-terminal truncations comprise 1, 2, 3, 4, 5, 6, 7, or 8 amino acid residues from the N-terminal end of the mature FGF21 polypeptide. Truncated FGF21 polypeptides having N-terminal truncations of fewer than 9 amino acid residues retain the ability of the mature FGF21 polypeptide to lower blood glucose in an individual. Accordingly, in particular embodiments, the present invention encompasses truncated forms of the mature FGF21 polypeptide or FGF21 protein variants having N-terminal truncations of 1, 2, 3, 4, 5, 6, 7, or 8 amino acid residues.

b. C-Terminal Truncations

In some embodiments of the present invention, C-terminal truncations comprise 1, 2, 3, 4, 5, 6, 7, 8, 9, 10, 11, or 12 amino acid residues from the C-terminal end of the mature FGF21 polypeptide. Truncated FGF21 polypeptides having C-terminal truncations of fewer than 13 amino acid residues exhibited an efficacy of at least 50% of the efficacy of wild-type FGF21 in an in vitro ELK-luciferase assay (Yie J. et al. FEBS Letts 583:19-24 (2009)), indicating that these FGF21 mutants retain the ability of the mature FGF21 polypeptide to lower blood glucose in an individual. Accordingly, in particular embodiments, the present invention encompasses truncated forms of the mature FGF21 polypeptide or FGF21 protein variants having C-terminal truncations of 1, 2, 3, 4, 5, 6, 7, 8, 9, 10, 11, or 12 amino acid residues.

c. N-Terminal and C-Terminal Truncations

In some embodiments of the present invention, truncated FGF21 polypeptides can have a combination of N-terminal and C-terminal truncations. Truncated FGF21 polypeptides having a combination of N-terminal and C-terminal truncations share the activity of corresponding truncated FGF21 polypeptides having either the N-terminal or C-terminal truncations alone. In other words, truncated FGF21 polypeptides having both N-terminal truncations of fewer than 9 amino acid residues and C-terminal truncations of fewer than 13 amino acid residues possess similar or greater blood glucose-lowering activity as truncated FGF21 polypeptides having N-terminal truncations of fewer than 9 amino acid residues or truncated FGF21 polypeptides having C-terminal truncations of fewer than 13 amino acid residues. Accordingly, in particular embodiments, the present invention encompasses truncated forms of the mature FGF21 polypeptide or FGF21 protein variants having both N-terminal truncations of 1, 2, 3, 4, 5, 6, 7, or 8 amino acid residues and C-terminal truncations of 1, 2, 3, 4, 5, 6, 7, 8, 9, 10, 11, or 12 amino acid residues.

As with all FGF21 variants of the present invention, truncated FGF21 polypeptides can optionally comprise an amino-terminal methionine residue, which can be introduced by directed mutation or as a result of a bacterial expression process.

The truncated FGF21 polypeptides of the present invention can be prepared as described in the examples described herein. Those of ordinary skill in the art, familiar with standard molecular biology techniques, can employ that knowledge, coupled with the instant disclosure, to make and use the truncated FGF21 polypeptides of the present invention. Standard techniques can be used for recombinant DNA, oligonucleotide synthesis, tissue culture, and transformation (e.g., electroporation, lipofection). See, e.g., Sambrook et al., Molecular Cloning: A Laboratory Manual, supra, which is incorporated herein by reference for any purpose. Enzymatic reactions and purification techniques can be performed according to manufacturer's specifications, as commonly accomplished in the art, or as described herein. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses; chemical analyses; pharmaceutical preparation, formulation, and delivery; and treatment of patients.

The truncated FGF21 polypeptides of the present invention can also be fused to another entity, which can impart additional properties to the truncated FGF21 polypeptide. In one embodiment of the present invention, a truncated FGF21 polypeptide can be fused to an IgG constant domain or fragment thereof (e.g., the Fc region), Human Serum Albumin (HSA), or albumin-binding polypeptides. Such fusion can be accomplished using known molecular biological methods and/or the guidance provided herein. The benefits of such fusion polypeptides, as well as methods for making such fusion polypeptides, are discussed in more detail herein.

FGF21 Fusion Proteins

As used herein, the term "FGF21 fusion polypeptide" or "FGF21 fusion protein" refers to a fusion of one or more amino acid residues (such as a heterologous protein or peptide) at the N-terminus or C-terminus of any FGF21 protein variant described herein.

Heterologous peptides and polypeptides include, but are not limited to, an epitope to allow for the detection and/or isolation of an FGF21 protein variant; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; a functional or non-functional antibody, or a heavy or light chain thereof; and a polypeptide which has an activity, such as a therapeutic activity, different from the FGF21 protein variants of the present invention. Also encompassed by the present invention are FGF21 mutants fused to human serum albumin (HSA).

FGF21 fusion proteins can be made by fusing heterologous sequences at either the N-terminus or at the C-terminus of an FGF21 protein variant. As described herein, a heterologous sequence can be an amino acid sequence or a non-amino acid-containing polymer. Heterologous sequences can be fused either directly to the FGF21 protein variant or via a linker or adapter molecule. A linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties.

a. Fc Fusions

In one embodiment of the present invention, an FGF21 protein variant is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas a Fab is short-lived (Capon et al., 1989, Nature 337: 525-31). When joined together with a therapeutic protein, an Fc domain can provide longer half-life or incorporate such functions as Fc receptor binding, protein A binding, complement fixation, and perhaps even placental transfer (Capon et al., 1989).

In vivo pharmacokinetic analysis indicated that human FGF21 has a short half-life of about 0.5 to 1 hours in mice due to rapid clearance and in vivo degradation. Therefore, to extend the half-life of FGF21 an Fc sequence was fused to the N- or C-terminal end of the FGF21 polypeptide. The fusion of an Fc region to wild-type FGF21, in particularly Fc fused to the N-terminus of wild-type FGF21, did not extend the half-life as expected, however, which led to an investigation of the proteolytic degradation of FGF21 in vivo and the identification of FGF21 mutants that were resistant to such degradation.

Throughout the disclosure, Fc-FGF21 refers to a fusion protein in which the Fc sequence is fused to the N-terminus of FGF21. Similarly, throughout the disclosure, FGF21-Fc refers to a fusion protein in which the Fc sequence is fused to the C-terminus of FGF21.

The resulting FGF21 fusion protein can be purified, for example, by the use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, or can be altered to improve certain qualities, such as therapeutic qualities, circulation time, or reduced aggregation.

Useful modifications of protein therapeutic agents by fusion with the "Fc" domain of an antibody are discussed in detail in International Publication No. WO 00/024782, which is hereby incorporated by reference in its entirety. This document discusses linkage to a "vehicle" such as polyethylene glycol (PEG), dextran, or an Fc region.

b. Fusion Protein Linkers

When forming the fusion proteins of the present invention, a linker can, but need not, be employed. When present, the linker's chemical structure may not critical, since it serves primarily as a spacer. The linker can be made up of amino acids linked together by peptide bonds. In some embodiments of the present invention, the linker is made up of from 1 to 20 amino acids linked by peptide bonds, wherein the amino acids are selected from the 20 naturally occurring amino acids. In various embodiments, the 1 to 20 amino acids are selected from the amino acids glycine, serine, alanine, proline, asparagine, glutamine, and lysine. In some embodiments, a linker is made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)). While a linker of 15 amino acid residues has been found to work particularly well for FGF21 fusion proteins, the present invention contemplates linkers of any length or composition.

The linkers described herein are exemplary, and linkers that are much longer and which include other residues are contemplated by the present invention. Non-peptide linkers are also contemplated by the present invention. For example, alkyl linkers such as can be used. These alkyl linkers can further be substituted by any non-sterically hindering group, including, but not limited to, a lower alkyl (e.g., C1-C6), lower acyl, halogen (e.g., Cl, Br), CN, NH2, or phenyl. An exemplary non-peptide linker is a polyethylene glycol linker, wherein the linker has a molecular weight of 100 to 5000 kD, for example, 100 to 500 kD.

Chemically-Modified FGF21 Mutants

Chemically modified forms of the FGF21 protein variants described herein, including the truncated forms of FGF21 described herein, can be prepared by one skilled in the art, given the disclosures described herein. Such chemically modified FGF21 mutants are altered such that the chemically modified FGF21 mutant is different from the unmodified FGF21 mutant, either in the type or location of the molecules naturally attached to the FGF21 mutant. Chemically modified FGF21 mutants can include molecules formed by the deletion of one or more naturally-attached chemical groups.

In one embodiment, FGF21 protein variants of the present invention can be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable. Non-water soluble polymers conjugated to FGF21 protein variants of the present invention also form an aspect of the invention.

Exemplary polymers each can be of any molecular weight and can be branched or unbranched. The polymers each typically have an average molecular weight of between about 2 kDa to about 100 kDa (the term "about" indicating that in preparations of a water-soluble polymer, some molecules will weigh more and some less than the stated molecular weight). The average molecular weight of each polymer is preferably between about 5 kDa and about 50 kDa, more preferably between about 12 kDa and about 40 kDa, and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-(C1-C10), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that can be used to prepare covalently attached FGF21 protein variant multimers. Also encompassed by the present invention are FGF21 mutants covalently attached to polysialic acid.

In some embodiments of the present invention, an FGF21 mutant is covalently, or chemically, modified to include one or more water-soluble polymers, including, but not limited to, polyethylene glycol (PEG), polyoxyethylene glycol, or polypropylene glycol. See, e.g., U.S. Pat. Nos. 4,640,835; 4,496,689; 4,301,144; 4,670,417; 4,791,192; and 4,179,337. In some embodiments of the present invention, an FGF21 mutant comprises one or more polymers, including, but not limited to, monomethoxy-polyethylene glycol, dextran, cellulose, another carbohydrate-based polymer, poly-(N-vinyl pyrrolidone)-polyethylene glycol, propylene glycol homopolymers, a polypropylene oxide/ethylene oxide co-polymer, polyoxyethylated polyols (e.g., glycerol), polyvinyl alcohol, or mixtures of such polymers.

In some embodiments of the present invention, an FGF21 mutant is covalently-modified with PEG subunits. In some embodiments, one or more water-soluble polymers are bonded at one or more specific positions (for example, at the N-terminus) of the FGF21 mutant. In some embodiments, one or more water-soluble polymers are randomly attached to one or more side chains of an FGF21 mutant. In some embodiments, PEG is used to improve the therapeutic capacity of an FGF21 mutant. Certain such methods are discussed, for example, in U.S. Pat. No. 6,133,426, which is hereby incorporated by reference for any purpose.

In embodiments of the present invention wherein the polymer is PEG, the PEG group can be of any convenient molecular weight, and can be linear or branched. The average molecular weight of the PEG group will preferably range from about 2 kD to about 100 kDa, and more preferably from about 5 kDa to about 50 kDa, e.g., 10, 20, 30, 40, or 50 kDa. The PEG groups will generally be attached to the FGF21 mutant via acylation or reductive alkylation through a reactive group on the PEG moiety (e.g., an aldehyde, amino, thiol, or ester group) to a reactive group on the FGF21 mutant (e.g., an aldehyde, amino, or ester group).

Branched PEG derivatives, also known as "Y-shaped" PEG derivatives, contain two linear methoxy PEG chain attached to a central core. The sterically bulky structure of these "Y-shaped" PEG derivatives will facilitate the single point attachment of the modified molecules. By way of example, three kinds of "Y-shaped" PEG derivatives are Y-NHS-40K (useful for amine PEGylation); Y-MAL-40K (useful for thiol PEGylation); and Y-ALD-40K (e.g., Y-AALD-40K and Y-PALD-40K)(useful for N-terminal PEGylation). For amine PEGylation, the "Y-shape" NHS ester will react with the amino group of lysine(s) or the N-terminal amine in biological active molecules to produce a stable amide linkage(s). This NHS ester will couple with the targeted molecules at pH 7-8. For thiol PEGylation, the "Y-shape" maleimide will react with the thiol groups in biological active molecules to generates a stable 3-thiosuccinimidyl ether linkage. This maleimide will couple with the targeted molecules at pH 5.0-6.5 in the presence of other functional groups. For N-terminal PEGylation, The "Y-shape" aldehyde will preferably react with the N-terminal amine in biological active molecules to produce a stable amine linkage in the presence of a reducing reagent such as sodium cyanoborohydride. This aldehyde will couple with the N-terminal amine of the targeted molecules at pH 5-8. Reagents for performing branched PEGylation are available through, e.g., JenKem Technology.

The PEGylation of a polypeptide, including the FGF21 mutants of the present invention, can be specifically carried out using any of the PEGylation reactions known in the art. Such reactions are described, for example, in the following references: Francis et al., 1992, Focus on Growth Factors 3: 4-10; European Patent Nos. 0 154 316 and 0 401 384; and U.S. Pat. No. 4,179,337. For example, PEGylation can be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono C1-C10 alkoxy or aryloxy derivatives thereof (see, e.g., U.S. Pat. No. 5,252,714).

In some embodiments of the present invention, a useful strategy for the attachment of the PEG group to a polypeptide involves combining, through the formation of a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water-soluble polymer that can be used for protein modification. Therefore, the FGF21 mutants of the present invention fused to a polysaccharide polymer form embodiments of the present invention. Dextrans are polysaccharide polymers comprised of individual subunits of glucose predominantly linked by alpha 1-6 linkages. The dextran itself is available in many molecular weight ranges, and is readily available in molecular weights from about 1 kD to about 70 kD. Dextran is a suitable water-soluble polymer for use as a vehicle by itself or in combination with another vehicle (e.g., Fc). See, e.g., International Publication No. WO 96/11953. The use of dextran conjugated to therapeutic or diagnostic immunoglobulins has been reported. See, e.g., European Patent Publication No. 0 315 456, which is hereby incorporated by reference. The present invention also encompasses the use of dextran of about 1 kD to about 20 kD.

In general, chemical modification can be performed under any suitable condition used to react a protein with an activated polymer molecule. Methods for preparing chemically modified polypeptides will generally comprise the steps of: (a) reacting the polypeptide with the activated polymer molecule (such as a reactive ester or aldehyde derivative of the polymer molecule) under conditions whereby a FGF21 protein variant becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment of the present invention, chemically modified FGF21 mutants can have a single polymer molecule moiety at the amino-terminus (see, e.g., U.S. Pat. No. 5,234,784)

In another embodiment of the present invention, FGF21 protein variants can be chemically coupled to biotin. The biotin/FGF21 protein variants are then allowed to bind to avidin, resulting in tetravalent avidin/biotin/FGF21 protein variants. FGF21 protein variants can also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that can be alleviated or modulated by the administration of the present chemically modified FGF21 mutants include those described herein for FGF21 protein variants. However, the chemically modified FGF21 mutants disclosed herein can have additional activities, enhanced or reduced biological activity, or other characteristics, such as increased or decreased half-life, as compared to unmodified FGF21 mutants.

Therapeutic Compositions of FGF21 Mutants and Administration Thereof

Therapeutic compositions comprising FGF21 mutants are within the scope of the present invention, and are specifically contemplated in light of the identification of several mutant FGF21 sequences exhibiting enhanced properties. Such FGF21 mutant pharmaceutical compositions can comprise a therapeutically effective amount of an FGF21 protein variant in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides; preferably sodium or potassium chloride; or mannitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage (see, e.g., Remington's Pharmaceutical Sciences, supra). Such compositions can influence the physical state, stability, rate of in vivo release, and rate of in vivo clearance of the FGF21 protein variant.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the present invention, FGF21 protein variant compositions can be prepared for storage by mixing the selected composition having the desired degree of purity with optional formulation agents (Remington's Pharmaceutical Sciences, supra) in the form of a lyophilized cake or an aqueous solution. Further, the FGF21 protein variant product can be formulated as a lyophilizate using appropriate excipients such as sucrose.

The FGF21 protein variant pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention can be in the form of a pyrogen-free, parenterally acceptable, aqueous solution comprising the desired FGF21 protein variant in a pharmaceutically acceptable vehicle. A particularly suitable vehicle for parenteral injection is sterile distilled water in which an FGF21 protein variant is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, an FGF21 protein variant can be formulated as a dry powder for inhalation. FGF21 protein variant inhalation solutions can also be formulated with a propellant for aerosol delivery. In yet another embodiment, solutions can be nebulized. Pulmonary administration is further described in International Publication No. WO 94/20069, which describes the pulmonary delivery of chemically modified proteins.

It is also contemplated that certain formulations can be administered orally. In one embodiment of the present invention, FGF21 protein variants that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the FGF21 protein variant. Diluents, flavorings, low melting point waxes, vegetable oils, lubricants, suspending agents, tablet disintegrating agents, and binders can also be employed.

Another pharmaceutical composition can involve an effective quantity of FGF21 protein variants in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional FGF21 protein variant pharmaceutical compositions will be evident to those skilled in the art, including formulations involving FGF21 protein variants in sustained- or controlled-delivery formulations. Techniques for formulating a variety of other sustained- or controlled-delivery means, such as liposome carriers, bio-erodible microparticles or porous beads and depot injections, are also known to those skilled in the art (see, e.g., International Publication No. WO 93/15722, which describes the controlled release of porous polymeric microparticles for the delivery of pharmaceutical compositions, and Wischke & Schwendeman, 2008, Int. J. Pharm. 364: 298-327, and Freiberg & Zhu, 2004, Int. J. Pharm. 282: 1-18, which discuss microsphere/microparticle preparation and use).

Additional examples of sustained-release preparations include semipermeable polymer matrices in the form of shaped articles, e.g. films, or microcapsules. Sustained release matrices can include polyesters, hydrogels, polylactides (U.S. Pat. No. 3,773,919 and European Patent No. 0 058 481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D-3-hydroxybutyric acid (European Patent No. 0 133 988). Sustained-release compositions can also include liposomes, which can be prepared by any of several methods known in the art. See, e.g., Epstein et al., 1985, Proc. Natl. Acad. Sci. U.S.A. 82: 3688-92; and European Patent Nos. 0 036 676, 0 088 046, and 0 143 949.

The FGF21 protein variant pharmaceutical composition to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

In a specific embodiment, the present invention is directed to kits for producing a single-dose administration unit. The kits can each contain both a first container having a dried protein and a second container having an aqueous formulation. Also included within the scope of this invention are kits containing single and multi-chambered pre-filled syringes (e.g., liquid syringes and lyosyringes).

The effective amount of an FGF21 protein variant pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the FGF21 protein variant is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg; or 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, up to about 100 mg/kg. In yet other embodiments, the dosage can be 50 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2000 µg/kg, 3000 µg/kg, 4000 µg/kg, 5000 µg/kg, 6000 µg/kg, 7000 µg/kg, 8000 µg/kg, 9000 µg/kg or 10 mg/kg.

The frequency of dosing will depend upon the pharmacokinetic parameters of the FGF21 protein variant in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by implantation device.

Alternatively or additionally, the composition can be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

Therapeutic Uses of FGF21 Polypeptide Mutants

FGF21 protein variants can be used to treat, diagnose, ameliorate, or prevent a number of diseases, disorders, or conditions, including, but not limited to metabolic disorders. In one embodiment, the metabolic disorder to be treated is diabetes, e.g., type 2 diabetes mellitus. In another embodiment, the metabolic disorder is obesity. Other embodiments include metabolic conditions or disorders such as type 1 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders.

In application, a disorder or condition such as type 1 or type 2 diabetes mellitus or obesity can be treated by administering an FGF21 protein variant as described herein to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the FGF21 mutant polypeptide. It will be apparent to those of skill in the art that a therapeutically effective dose of FGF21 mutant polypeptide will depend, inter alia, upon the administration schedule, the unit dose of antigen administered, whether the nucleic acid molecule or polypeptide is administered in combination with other therapeutic agents, the immune status and the health of the recipient. The term "therapeutically effective dose," as used herein, means that amount of FGF21 mutant polypeptide that elicits the biological or medicinal response in a tissue system, animal, or human being sought by a researcher, medical doctor, or other clinician, which includes alleviation of the symptoms of the disease or disorder being treated.

Pharmaceutical Compositions

The present invention also provides pharmaceutical compositions comprising one or more of the FGF21 variants or mutants described herein and a pharmaceutically acceptable carrier. In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

Fusion Proteins and FGF21-Derived Peptidic Compounds

In another embodiment, the FGF21 variants of the present invention can be made into a fusion protein or peptidic compound derived from the FGF21 variants amino acid sequences. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into FGF21 variants, or conjugating FGF21 variants to poly(ethylene glycol)(PEG; pegylation), e.g., via lysine-monopegylation or cysteine-monopegylation. Such techniques have proven to be beneficial in prolonging the half-life of therapeutic protein drugs. It is expected that pegylation of the FGF21 variants of the invention may result in similar pharmaceutical advantages.

In addition, pegylation can be achieved in any part of a polypeptide of the invention by the introduction of a normatural amino acid. Certain normatural amino acids can be introduced by the technology described in Deiters et al., J Am Chem Soc 125:11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the normatural amino acid of choice. Particular normatural amino acids that are beneficial for purpose of conjugating moieties to the polypeptides of the invention include those with acetylene and azido side chains. The FGF21 variants containing these novel amino acids can then be pegylated at these chosen sites in the protein.

EXAMPLES

Example 1

Preparation and PEGylation of FGF21 Variant Proteins

Expression constructs for FGF21 variants: The FGF21 variants were cloned into the modified *E. coli* expression vector pET30a, described by Achmuller et al. (2007) (Nature Methods 4:1037-1043), to generate in-frame fusions to a hexa-histidine tag followed by the N$^{pro}$-EDDIE tag at the N-terminus of FGF21 (aa 33-209).

Expression and purification of FGF21 variants: The pET30a-His-N$^{pro}$-EDDIE-FGF21 expression plasmid was transformed into *E. coli* BL21 Star (DE3) competent cells (Invitrogen). Overnight growth from a single colony of freshly transformed cells was carried out in 50 mL of Terrific Broth (TB) containing 50 µg/mL of kanamycin at 37° C. The pre-culture was transferred into 1 L of TB medium with kanamycin and cultured in baffled flasks at 37° C. with shaking at 250 rpm. After 6 hour of culture, expression of FGF21 was induced by the addition of IPTG at a final concentration of 1 mM, and the cultures were grown overnight at 37° C. The cells were then harvested and resuspended into 50 mL of ice-cold lysis buffer; 50 mM Tris-HCl, pH 8, 150 mM NaCl, 1 mM EDTA, followed by lysis using a Microfluidizer™.

Inclusion bodies (IBs) were precipitated by centrifugation at 30,000×g for 1 hour at 4° C. The IBs were washed with 50 mM Tris-HCl, pH 8, 150 mM NaCl and then dissolved into 30 mL of dissolving buffer; 10 mM Tris-HCl, pH8, 100 mM NaH$_2$PO$_4$, 6 M GnHCl. The dissolved IBs were clarified by centrifugation at 30,000×g for 1 hour at 25° C. The IB solution was loaded onto a 5 mL column of Ni-NTA high performance resin (GE Healthcare) equilibrated with the dissolving buffer. Proteins bound to the resin were eluted by decreasing the pH to 4.5. The eluate was conditioned by adjusting pH and adding dithiothreitol (DTT) at a concentration of 20 mM. The conditioned eluate was slowly diluted into 1 L of refolding buffer; 50 mM Tris-HCl, pH 8, 0.5 M arginine, 20 mM DTT, followed by incubation for 2 days at 4° C. The diluted sample was concentrated and buffer-exchanged into 20 mM Tris-HCl, pH 9 using an ultrafiltration method. The concentrated sample was loaded onto a 10 mL column of Q sepharose fast flow resin (GE Healthcare) equilibrated with 20 mM Tri-HCl (pH9).

After washing the resin with the equilibration buffer, proteins bound to the resin were eluted with 20 mM Tris-HCl, pH 9, 500 mM NaCl. To remove the cleaved off His-N$^{pro}$ fusion fragment and any uncleaved fusion protein from the refolded FGF21 protein, the eluate was loaded onto a 5 mL column of Ni-NTA high performance resin equilibrated with 20 mM Tris, pH 8.0, 50 mM imidazole, and the flow-through fraction containing FGF21 was collected. To reduce endotoxin levels, the FGF21 fraction was treated with an EndoTrap HD resin (Hyglos) equilibrated with 10 mM Tris, pH 8, 50 mM imidazole, 500 mM NaCl, 1 mM CaCl$_2$. The low-endotoxin sample was dialyzed against PBS and then sterilized with a 0.22 µm filter. The purified FGF21 protein was snap-frozen in liquid nitrogen and stored at −80° C. Protein concentration was determined by absorbance at 280 nm using 9362 M−1 cm−1 as the molar extinction coefficient for FGF21. Protein purity and integrity were determined by HPLC, SDS-PAGE and liquid chromatography-mass spectrometry.

Cysteine PEGylation of FGF21 variants: hsFGF21 (R154C) variants have tendency to dimerize via the engineered cysteine; therefore, prior to PEGylation the protein solution (typically 5 mg/ml in Tris buffer) was mildly reduced with 5 mM mercaptoethylamine for 30 minutes on ice and immediately desalted in 20 mM Tris, pH 7. The freshly reduced protein (typically 3 mg/ml) was then immediately PEGylated with 1.5 equivalent of 40 kDa branched maleimido-PEG reagent (NOF catalog #GL2-400MA from the Sunbright series) for 3 hours on ice. The PEGylated protein was finally purified by anion exchange chromatography (MonoQ) with overall yields of about 25%.

N-terminal PEGylation of FGF21 variants: The final concentration of the FGF21 variant and the 40 kDa branched PEG reagent (NOF catalog #GL2-400AL3 from the Sunbright series; 3:1 molar ratio to FGF21) was 3-4 mg/mL and 9-12 mg/mL, respectively. The buffer was 50 mM sodium acetate, pH 6.0, 25 mM sodium chloride and 40 mM sodium cyanoborohydride. The reaction mixtures were tumbled gently at 4° C. for 44 hr and the reaction conversion was monitored over several time points. Approximate conversion at 20 hr was 50% and at 44 hr was 70%.

Example 2

Generation of human FGF21 Disulfide Variants

Cloning library: The vector pGAPZalphaA (Invitrogen, Carlsbad, Calif.) was modified by adding a β-lactamase expression cassette in the vector's unique BamHI site. The β-lactamase expression cassette was generated as described by Hribar, et al (2008) BioTechniques 44:477-84. The human FGF21 cDNA encoding amino acids 33 to 209 was cloned into the modified pGAPZ alphaA vector after the glyceraldehyde-3-phosphate dehydrogenase (GAP) promoter in frame with N-terminal sequences including an alpha mating factor secretion signal sequence, a six histidine affinity purification tag, and a Tobacco Etch Virus (TEV) protease recognition sequence. A library of hFGF21 constructs was generated with each construct having Cys 103 and Cys121 that are in the wild-type sequence as well as two wild-type amino acids that were mutated to cysteines. The library was made by generating PCR fragments of the hFGF21 amino acid 33-209 coding region with primers that encoded a cysteine in place of the wild-type amino acid. The PCR fragments were designed so that they shared sixteen base pairs of identical sequence with each other or the linearized modified pGAPZalphaA vector so that they could be joined using the In-Fusion enzyme (Takara Bio Co USA). Each construct was sequence verified before it was used for yeast strain generation.

Generating yeast strains: The *Pichia pastoris* yeast strain SMD1168H (Invitrogen) was modified by disrupting the YPS1 gene as described by Yao et al (2009) J. Biotechnol. January 15; 139(2):131-6. The modified strain (SMD1168H delta YPS1) had resistance to 300 μg/mL blasticidin. About 5-10 μg of sequence verified plasmid DNA was digested with Avr II and was mixed with SMD1168H delta YPS1 cells that were prepared according to Invitrogen's manual for pGAPZα-A. The cells mixed with a linearized plasmid in a 0.2 cm cuvette (Bio-Rad, Hercules, Calif.). The cuvette with the cells and linearized plasmid was incubated on ice for 5 mM The cuvette was pulsed using a Gene Pulser-II (Bio-Rad) with voltage set to 1.5 kV, the capacitor set to 25 μF, and the pulse controller set to 400 Ohms.

Immediately after the pulse, 1 mL of ice-cold 1 M sorbitol was added to the cuvette, and its contents were transferred to a sterile 15 mL tube. The tube was incubated at 30° C. without shaking for 2 h. The electroporated cells were spread on YPDS (1% yeast extract, 2% peptone, 2% dextrose, 1M sorbitol, and 2% agar) plates containing 100 μg/mL zeocin (zeo). The plates were incubated from 3-10 days at 30° C. until colonies formed. Twenty four colonies of each construct were picked and used to inoculate 1 mL YPD growth medium containing 100 μg/mL zeocin in a 96-well deep-well plate. The plate was incubated overnight at 30° C. in a shaker (Sheldon Manufacturing, Cornelius, Oreg.) at 900 RPM. A 10 μL aliquot of each culture was removed and diluted into 990 μL of PBS (pH 7.4) in a 96-well deep-well plate.

For colorimetric determination of β-lactamase activity, 50 μL of 1:100 diluted culture was transferred into a 96-well microtiter plate. Nitrocefin (1 mg; EMD Chemicals, Gibbstown, N.J.) was dissolved in 100 μL DMSO and diluted into 1.9 mL PBS to obtain a working solution of 1 mM. The nitrocefin working solution (50 uL) was added into each well for a final concentration of 500 uM. After the addition of nitrocefin, the plate was incubated at room temperature (RT) in the dark for 5 min. Absorbance at 492 nm was measured on a Spectramax Plus microtiter plate reader (Molecular Devices, Sunnyvale, Calif.) to determine the β-lactamase activity. Glycerol stocks of the two strains with the highest β-lactamase activity for each construct were made and stored at −80° C.

Small scale expression and purification of hFGF21 disulfide variants: The hFGF21 disulfide variant glycerol stocks from the two strains with the highest β-lactamase specific activity for each construct were used to inoculate 1 mL of Buffered Complex Glucose Medium (1% yeast extract, 2% peptone, 100 mM potassium phosphate, pH 6.0, 1.34% YNB, 4×10-5% biotin, 2% glucose, and 2% casamino acids) in 96-well deep-well plates. The cultures were grown at 30° C. with shaking at 900 RPM (Sheldon Manufacturing, Cornelius, Oreg.) for approximately 48 h until the cell growth reached saturation. An aliquot of the saturated culture (25 uL) was used to inoculate 5 mL of Buffered Complex Glucose Medium in 24-well deep-well plates. The plates were incubated overnight at 30° C. in a shaker (Sheldon Manufacturing, Cornelius, Oreg.) at 350 RPM. After about 24 h the plates were centrifuged at 2500×g for 15 min. The media was aspirated off of the pelleted cells and added to an Amicon ultra-15 centrifugal filter unit (Millipore, Billerica, Mass.) with a 10 kDa cutoff membrane. Ten mL of PBS, pH 7.4 containing 10 mM imidazole and 1× Halt EDTA-free protease inhibitor cocktail (Thermo, Rockford, Ill.) was added to the media in the concentrator to bring the total volume to 15 mL.

The filter unit was centrifuged at 4000 RMP in a Sorvall Legend RT plus centrifuge (Thermo) for 30 min The concentrator flow through was discarded and about 13 mL of PBS, pH 7.4 was added to the concentrated media. The filter unit was centrifuged again at 4000 RMP for 30 min. The concentrated buffer exchanged sample was loaded onto a nickel-nitrilotriacetic acid (Ni-NTA) spin column (Qiagen, Valencia, Calif.). The column was centrifuged at 270×g (1600 rpm) in a Sorvall Legend Micro 21R centrifuge (Thermo) for 5 min, and then washed two times with 600 uL of PBS, pH 7.4 containing 10 mM imidazole. The 6 HIS tagged hFGF21 variants were eluted with 200 uL of PBS, pH 7.4 containing 300 mM imidazole.

Medium scale expression and purification of hFGF21 disulfide variants: The hFGF21 disulfide variant glycerol stocks from the strains that expressed hFGF21 disulfide variants with the highest activity, when tested in the two point pERK cellular assay (10 and 100 nM), were used to inoculate 5 mL of Buffered Complex Glucose Medium (1% yeast extract, 2% peptone, 100 mM potassium phosphate, pH 6.0, 1.34% YNB, 4×10-5% biotin, 2% glucose, and 2% casamino acids) containing 100 μg/mL zeocin in a 50 mL sterile tube. The cultures were grown at 30° C. with shaking at 250 RPM for approximately 48 h until the cell growth reached saturation. An aliquot of the saturated culture (50 uL) was used to inoculate 100 mL of Buffered Complex Glucose Medium in a 250 mL Ultra Yield flask (Thomson Instrument Co, Oceanside, Calif.). The flasks were incubated overnight at 30° C. in a shaker at 300 RPM. After about 24 h the cells were centrifuged at 2500×g for 15 min. The media (80 mL) was aspirated off of the pelleted cells and added to a Centricon-70 centrifugal filter unit (Millipore, Billerica, Mass.) with a 10 kDa cutoff membrane. The filter unit was centrifuged at 4000 RMP in a Sorvall Legend RT plus centrifuge (Thermo) for 30 mM The remaining clarified media (about 20 mL) was added to a Centricon-70 centrifugal filter and the total volume in the filter was increased to 80 mL by adding PBS, pH7.4 containing 10 mM imidazole and 1×EDTA-free Halt protease inhibitor cocktail. The filter unit was centrifuged again at 4000 rpm for 30 mM. The volume of the concentrated media in the filter unit was increased to 80 mL by adding PBS, pH 7.4 containing 10 mM. The filter unit was centrifuged again at 4000 rpm for 30 min.

The concentrated buffer exchanged sample was loaded onto a 1 mL His-Gravitrap column (GE Lifesciences, Piscataway, N.J.) that was pre-equilibrated with PBS, pH 7.4 containing 10 mM imidazole. The column was washed with 10 mL of PBS, pH 7.4 containing 20 mM imidazole. The 6HIS tagged hFGF21 variants were eluted with 2.5 mL of PBS, pH 7.4 containing 300 mM imidazole. The 2.5 mL of elution buffer was applied to a 10 mL PD-10 desalting column that was pre-equilibrated with 25 mL of PBS, pH 7.4 containing 10 mM imidazole. The 6HIS tagged disulfide variants were eluted from the desalting column with 3.5 mL of PBS, pH 7.4 containing 10 mM imidazole.

The 6HIS tag was removed from the desalted affinity-purified hFGF21 disulfide variants by adding ProTEV protease (250 units; Promega, Madison, Wis.) and incubating the sample at room temperature for 2 h and overnight at 4° C. The tag-cleaved hFGF21 disulfide variants loaded onto a 1 mL His-Gravitrap column that was pre-equilibrated with PBS, pH 7.4 containing 10 mM imidazole. The flow-through containing the tag-cleaved hFGF21 disulfide variants was collected. The His-Gravitrap column was washed with 5 mL with PBS, pH 7.4 containing 10 mM imidazole. The column flow through was collected and added to the flow through from the tag cleavage reaction. The combined flow-through samples (about 8.5 mL) were concentrated to about 1 mL with Amicon ultra-15 centrifugal filter with a 10 kDa cutoff membranes. The concentrated hFGF21 disulfide variants were frozen at −80° C. until being assayed in the pERK cellular assay.

Example 3

Measuring 2-Deoxyglucose (2-DOG) Uptake

More recently, FGF21 has been shown to stimulate glucose-uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose-dependent manner, thus, providing the basis for the use of FGF21 as a therapy for treating diabetes and obesity (see, e.g., patent publication WO03/011213, and Kharitonenkov et al., (2005) Jour. of Clinical Invest. 115:1627-1635). Also, FGF21 was observed to stimulate tyrosine phosphorylation of FGFR-1 and FGFR-2 in 3T3-L1 adipocytes.

T3-L1 fibroblasts were purchased from ATCC (Catalog #CL173). The cells were grown to confluency in 150 cm petri-dish and were maintained in DMEM with high glucose (Invitrogen #11995065) supplemented with 10% Fetal Bovine Serum and 1% penicillin-streptomycin for an additional 4 days. Cells were then differentiated in the above media supplemented with 4 µg/ml insulin (Sigma Catalog #I-5500), 115 µg/ml IBMX (Sigma Catalog #15879) and 0.0975 µg/ml dexamethasone (Sigma Catalog #D1756) for 3 days after which the differentiation media was replaced with complete DMEM. One plate of differentiated 3T3-L1 adipocytes were seeded on four 96-well plates the day after medium replacement.

The adipocytes were then treated with FGF21-WT and FGF21 variants (see Table 2 for list of variants; 30 µM to 100 nM is the typical concentration range used) overnight in complete medium. The adipocytes treated with FGF21 samples are serum starved in 50 µl per well KRH buffer (0.75% NaCl; 0.038% KCl; 0.0196% CaCl2; 0.032% MgSO4; 0.025M Hepes, pH 7.5; 0.5% BSA; 2 mM sodium pyruvate) for 2 hours. The wells for blank were added with 1 µl (final concentration 5 µg/ml) cytochalasin B for 15 min. [3H]-2-DOG (20.6 mci/mmol, 1 mci/ml), which was diluted 1:20 in 5.1 mM cold 2-DOG, 1 µl diluted 2-DOG per well was added to the cells and incubated for 5 min. The cells were washed with 100 µl/well KRH buffer three times. 40 µl/well 1% SDS were added to cells and the cells were shaken for at least 10 min. 200 µl/well scintillation fluid were added and the plates were shaken overnight and read in beta-microplate reader. The values obtained from an entire column/row which were treated with cytochalasin B was averaged and subtracted from all other values. The data were analyzed by GraphPad prism software, the results of which are summarized in Table 2.

TABLE 2

Summary of EC50 values and relative potencies (Fold-WT) of FGF21 WT and FGF21 variants in the 3T3-L1 adipocyte 2-deoxy-glucose (2-DOG) uptake assay.

| Variant ID | Standardized name | EC50 (nM) | Fold-WT (1) | N |
|---|---|---|---|---|
| V5 | hFGF21(33-209)-V5 | 3.3 | 1.5 | 1 |
| V7 | hFGF21(33-209)-V7 | 3.9 | 1.8 | 1 |
| V8 | hFGF21(33-209)-V8 | 1.8 | 0.8 | 1 |
| V9 | hFGF21(33-209)-V9 | 3.1 | 1.0 | 1 |
| V10 | hFGF21(33-209)-V10 | 2.8 | 1.3 | 1 |
| V11 | hFGF21(33-209)-V11 | 3.4 | 1.6 | 1 |
| V12 | hFGF21(33-209)-V12 | 3.2 | 1.5 | 1 |
| V13 | hFGF21(33-209)-V13 | 2.9 | 1.3 | 1 |
| V14 | hFGF21(33-209)-V14-pool1 | 0.56 | 1.0 | 7 |
| V14-N130D | hFGF21(33-209)-V14-pool2 | 0.60 | 1.5 | 4 |
| V14-N-PEG | hFGF21(33-209)-V14pool1-N-40 kDa bPEG-AL | 5.7 | 8.8 | 3 |
| V14-R154C, L174P | hFGF21(33-209)-V14-R154C, L174P | 0.58 | 1.1 | 6 |
| V14-L174P, R154C-PEG | hFGF21(33-209)-V14-L174P, R154C-40 kDa bPEG-MA | 4.3 | 8.9 | 6 |
| V15 | hFGF21(33-209)-V15 | 3.2 | 1.5 | 1 |
| V16 | hFGF21(33-209)-V16 | 3.1 | 1.4 | 1 |
| V18 | hFGF21(33-209)-V18 | 2.6 | 0.8 | 1 |
| V53 | hFGF21(33-209)-V53 | 0.78 | 1.4 | 3 |
| V54 | hFGF21(33-209)-V54 | 2.5 | 1.1 | 1 |
| V55 | hFGF21(33-209)-V55 | 3.7 | 1.7 | 1 |
| V56 | hFGF21(33-209)-V56 | 3.0 | 1.3 | 1 |
| V57 | hFGF21(33-209)-V57 | 0.60 | 0.69 | 4 |
| V58 | hFGF21(33-209)-V58 | 0.31 | 1.1 | 1 |
| V59 | hFGF21(33-209)-V59 | 0.67 | 0.69 | 3 |
| V60 | hFGF21(33-209)-V60 | 1.0 | 0.5 | 1 |
| V61 | hFGF21(33-209)-V61 | 1.9 | 0.9 | 1 |
| V62 | hFGF21(33-209)-V62 | 1.5 | 0.7 | 1 |
| V63 | hFGF21(33-209)-V63 | 1.9 | 0.9 | 1 |
| V64 | hFGF21(33-209)-V64 | 0.56 | 0.3 | 1 |
| V73 | hFGF21(33-209)-V73 | 1.1 | 2.8 | 2 |
| V73-N-PEG | hFGF21(33-209)-V73-N-40 kDa bPEG-AL | 0.89 | 1.8 | 2 |
| V76 | hFGF21(33-209)-V76 | 0.77 | 1.0 | 1 |
| V76-154C-PEG | hFGF21(33-209)-V76-154C-40 kDa bPEG-MA | 1.8 | 4.5 | 2 |
| V79 | hFGF21(33-209)-V79 | 2.3 | 2.3 | 1 |
| V80 | hFGF21(33-209)-V80 | 0.66 | 0.7 | 1 |
| V81 | hFGF21(33-209)-V81 | 0.83 | 0.8 | 1 |
| V82 | hFGF21(33-209)-V82 | 10 | 2.0 | 1 |
| V83 | hFGF21(33-209)-V83 | 7.4 | 1.5 | 1 |
| V84 | hFGF21(33-209)-V84 | 1.6 | 2.8 | 3 |
| V85 | hFGF21(33-209)-V85 | 1.1 | 1.5 | 1 |
| WT | hFGF21(33-209)-WT-CH | 0.99 | 1.0 | 20 |
| WT-L174P | hFGF21(33-209)-WT-AM | 2.2 | 1.5 | 3 |
| WT-N-PEG | hFGF21(33-209)-WT-N-40 kDa bPEG-AL | 1.1 | 3.1 | 2 |
| WT-R154C | hFGF21(33-209)-WT-R154C | 0.42 | 1.2 | 2 |
| WT-R154C-PEG | hFGF21(33-209)-WT-R154C-40 kDa bPEG-MA | 1.4 | 3.3 | 2 |

(1) "Fold-WT" is ratio of EC50 value of the FGF21 variant to FGF21-WT carried out "head to head" in the same experiment.

Example 4 pERK In Cell Western (ICW) Assay

HEK293 cells stably transfected with human β-klotho were cultured in DMEM high glucose, 10% FBS, 1% PS and 600 ng/ml G418 are seeded in poly-D-lysine coated 96-well plates (BD bioscience, 356640) at 30,000 cells per well overnight. The cells were serum starved in DMEM high glucose, 0.5% BSA and 10 mM HEPES for 4 hours. WT FGF21 and the FGF21 variants (see Table 3 for list of variants) were diluted to various concentrations (100 pM to 300 nM is the typical concentration range used) in starvation medium. The cells were stimulated with FGF21 for 10 min. Following FGF21 stimulation, the media was aspirated from the wells and the cells were washed once with 100 μl cold PBS and then fixed with 100 μl of 4% formaldehyde for 15 mins at RT and followed by an additional 10 mins incubation with 100 μl ice-cold methanol.

After fixation, the cells were washed with 0.3% Triton X-100 in PBS four times, 5 mins each. 150 μl Odyssey Blocking Buffer was added to the permeabilized cells at room temperature for 1.5 hours. Phospho-ERK (pERK) antibody was diluted to a concentration of 0.17 μg/ml (1:200 dilution, or the dilutions indicated), and total-ERK (tERK) antibody was diluted to a concentration of 2.2 μg/ml (1:200 dilution, or the dilutions indicated) in Odyssey Blocking Buffer. 50 μl was added to every well, omitting one column which was only treated with secondary antibody to normalize for background. The plate was covered with the wet paper tower and lid to prevent evaporation and then incubated at 4° C. overnight.

Afterwards, the primary antibody was aspirated and the cells were washed four times with 0.3% Tween 20 in PBS for 5 mins each. During the washing, the secondary antibody reaction mixture was prepared in Odyssey Blocking Buffer containing 1:1000-diluted (or the dilutions indicated) goat anti-mouse Alexa 680 and 1:1000-diluted (or the dilutions indicated) IRDye800 goat anti-rabbit antibody. Once the washing was completed, 40 μl of the reaction mixture was added to each well. Plates were covered with black lid to protect the secondary antibody from light, and plates were incubated at RT for 1 hr on a shaker. Finally, the cells were washed again four times with 0.3% Tween 20 in PBS for 5 min each and then scanned on the LI-COR Bioscience Odyssey Infrared Imaging System (Li-Cor Biosciences, Lincoln, Nebr.) in the 700 nm (red) and 800 nm (green) channels. Alexa 680 stained the tERK with far-red fluorescence (emission wavelength 668 nm), while IRDye800 stained the pERK with green fluorescence (emission wavelength 800 nm). To eliminate the fluorescent background, the values obtained from an entire column/row which was treated with only secondary antibody was averaged and subtracted from all other values obtained from the plate. For normalization of the amount of pERK present in each sample, the values for pERK in each well was divided by the values of tERK. The data were analyzed by GraphPad prism software, the results of which are summarized in Table 3.

TABLE 3

Summary of EC50 values and relative potencies (Fold-WT) of FGF21 WT and FGF21 variants in the pERK cellular assay using HEK293 cells stably transfected with human β-klotho.

| Variant ID | Standardized Name | EC50 (nM) | Fold-WT (1) | N |
|---|---|---|---|---|
| V5 | hFGF21(33-209)-V5 | 26 | 9.3 | 1 |
| V7 | hFGF21(33-209)-V7 | 19 | 6.8 | 1 |
| V8 | hFGF21(33-209)-V8 | 14 | 5.0 | 1 |
| V9 | hFGF21(33-209)-V9 | 13 | 2.4 | 1 |
| V10 | hFGF21(33-209)-V10 | 18 | 3.3 | 1 |
| V11 | hFGF21(33-209)-V11 | 28 | 18 | 1 |
| V12 | hFGF21(33-209)-V12 | 14 | 5.0 | 1 |
| V13 | hFGF21(33-209)-V13 | 11 | 4.0 | 1 |
| V14 | hFGF21(33-209)-V14-pool1 | 6.7 | 1.4 | 6 |
| V14-N130D | hFGF21(33-209)-V14-pool2 | 5.3 | 1.4 | 3 |
| V14-N-PEG | hFGF21(33-209)-V14pool 1-N-40 kDa bPEG-AL | 107 | 22 | 5 |
| V14-R154C, L174P | hFGF21(33-209)-V14-R154C, L174P | 6.7 | 1.0 | 3 |
| V14-L174P, R154C-PEG | hFGF21(33-209)-V14-L174P, R154C-40 kDa bPEG-MA | 21 | 3.3 | 3 |
| V15 | hFGF21(33-209)-V15 | 3.3 | 1.2 | 1 |

TABLE 3-continued

Summary of EC50 values and relative potencies (Fold-WT) of FGF21 WT and FGF21 variants in the pERK cellular assay using HEK293 cells stably transfected with human β-klotho.

| Variant ID | Standardized Name | EC50 (nM) | Fold-WT (1) | N |
|---|---|---|---|---|
| V16 | hFGF21(33-209)-V16 | 11 | 6.5 | 1 |
| V18 | hFGF21(33-209)-V18 | 15 | 2.7 | 1 |
| V52 | hFGF21(33-209)-V52 | 66 | 94 | 1 |
| V53 | hFGF21(33-209)-V53 | 4.2 | 1.3 | 3 |
| V54 | hFGF21(33-209)-V54 | 25 | 9.2 | 1 |
| V55 | hFGF21(33-209)-V55 | 34 | 13 | 1 |
| V56 | hFGF21(33-209)-V56 | 37 | 14 | 1 |
| V57 | hFGF21(33-209)-V57 | 22 | 5.4 | 3 |
| V58 | hFGF21(33-209)-V58 | 3.6 | 2.6 | 1 |
| V59 | hFGF21(33-209)-V59 | 6.5 | 1.6 | 3 |
| V60 | hFGF21(33-209)-V60 | 7.6 | 2.2 | 1 |
| V61 | hFGF21(33-209)-V61 | 22 | 6.3 | 1 |
| V62 | hFGF21(33-209)-V62 | 24 | 6.8 | 1 |
| V63 | hFGF21(33-209)-V63 | 13 | 3.7 | 1 |
| V64 | hFGF21(33-209)-V64 | 2.9 | 0.80 | 1 |
| V73 | hFGF21(33-209)-V73 | 5.8 | 1.7 | 3 |
| V73-N-PEG | hFGF21(33-209)-V73-N-40 kDa bPEG-AL | 191 | 66 | 2 |
| V76 | hFGF21(33-209)-V76 | 3.4 | 0.47 | 3 |
| V76-154C-PEG | hFGF21(33-209)-V76-154C-40 kDa-bPEG-MA | 8.3 | 2.4 | 4 |
| V79 | hFGF21(33-209)-V79 | 2.2 | 0.40 | 1 |
| V80 | hFGF21(33-209)-V80 | 2.2 | 0.40 | 1 |
| V81 | hFGF21(33-209)-V81 | 11 | 2.1 | 1 |
| V82 | hFGF21(33-209)-V82 | 1.5 | 2.7 | 1 |
| V83 | hFGF21(33-209)-V83 | 0.21 | 0.38 | 1 |
| V84 | hFGF21(33-209)-V84 | 4.5 | 1.1 | 3 |
| V85 | hFGF21(33-209)-V85 | 2.0 | 0.30 | 1 |
| V86 | hFGF21(33-209)-V86 | 8.5 | 4.5 | 1 |
| V87 | hFGF21(33-209)-V87 | 1.9 | 1.6 | 1 |
| WT | hFGF21(33-209)-WT-CH | 7.4 | 1.0 | 33 |
| WT-R154C | hFGF21(33-209)-WT-R154C | 4.2 | 1.3 | 3 |
| WT-R154C-PEG | hFGF21(33-209)-WT-R154C-40 kDa bPEG-MA | 9.0 | 2.9 | 3 |
| WT-N-PEG | hFGF21(33-209)-WT-N-40 kDa bPEG-AL | 20 | 6.3 | 3 |
| WT-L174P | hFGF21(33-209)-WT-AM | 5.7 | 1.5 | 3 |

(1) "Fold-WT" is ratio of the EC50 value of the FGF21 variant to the EC50 value of FGF21-WT carried out "head to head" in the same experiment.

Example 5

In vivo Tests of FGF21 and FGF21 Variants—Pharmacodynamics and Plasma Exposures

The ob/ob mouse is a mouse model for type 2 diabetes. The mice lack functional leptin and are characterized by hyperglycemia, insulin resistance, hyerphagia, hepatic steatosis and obesity. Male ob/ob mice (10-13 weeks old) were used to measure the effect on blood glucose of the following: (1) wild type FGF21, (2) FGF21 variants, (3) PEGylated wild type FGF21, and (4) PEGylated FGF21 variants.

The wild type FGF21, variant FGF21 or PBS vehicle were administered s.c. at 1 mg/kg and 4 ml/kg once daily for 5 days. On the first day of the study, tail blood glucose and body weight were measured and mice were allocated into different groups (n=8 per group) with mean glucose and body weight matched among the groups. Blood glucose was measured using a glucometer (OneTouch) on days 1, 3 and 5 before dosing and 2 and 4 hours after dosing. The results of these studies are summarized in Table 4.

TABLE 4

Percent reduction of total glucose AUC by FGF21 variants during 5-day screening studies in ob/ob mice.

| Variant ID | Dose (mg/kg) | Glucose AUC reduction vs. vehicle | Fold change over WT | Variant ID | Dose (mg/kg) | Glucose AUC reduction vs. vehicle | Fold change over WT (1) |
|---|---|---|---|---|---|---|---|
| V1 | 1 mg/kg | −30% | 0.86 | V57 | 1 mg/kg | −18% | 0.90 |
| V5 | 1 mg/kg | −25% | 1.19 | V58 | 1 mg/kg | −20% | 0.65 |
| V7 | 1 mg/kg | −25% | 1.19 | V59 | 1 mg/kg | −22% | 0.69 |
| V8 | 1 mg/kg | −16% | 0.76 | V60 | 1 mg/kg | −21% | 1.05 |
| V9 | 1 mg/kg | −20% | 0.95 | V61 | 1 mg/kg | −5% | 0.25 |
| V10 | 1 mg/kg | −31% | 1.48 | V62 | 1 mg/kg | −2% | 0.10 |
| V11 | 1 mg/kg | −29% | 0.83 | V63 | 1 mg/kg | −13% | 0.65 |
| V12 | 1 mg/kg | −31% | 0.89 | V73 | 1 mg/kg | −26% | 0.74 |
| V13 | 1 mg/kg | −27% | 0.87 | V76 exp1 | 1 mg/kg | −30% | 0.86 |
| V14 exp1 | 1 mg/kg | −33% | 0.94 | V76 exp2 | 1 mg/kg | −16% | 1.45 |
| V14 exp2 | 1 mg/kg | −37% | 1.06 | V79 | 1 mg/kg | −30% | 1.15 |
| V14 exp3 | 1 mg/kg | −36% | 1.16 | V80 | 1 mg/kg | −23% | 0.88 |
| V14-R154C, L174P | 1 mg/kg | −30% | 0.97 | V81 | 1 mg/kg | −24% | 0.92 |
| V15 | 1 mg/kg | −26% | 0.74 | V82 | 1 mg/kg | −31% | 1.19 |
| V16 | 1 mg/kg | −24% | 0.69 | V83 exp1 | 1 mg/kg | −32% | 1.23 |
| V18 | 1 mg/kg | −20% | 0.95 | V83 exp2 | 1 mg/kg | −30% | 2.73 |
| V53 | 1 mg/kg | −32% | 1.03 | V84 | 1 mg/kg | −23% | 0.88 |
| V54 | 1 mg/kg | −25% | 0.78 | V85 | 1 mg/kg | −16% | 1.45 |
| V55 | 1 mg/kg | −22% | 0.69 | WT-L174P | 1 mg/kg | −28% | 0.92 |
| V56 | 1 mg/kg | −20% | 0.63 | WT | 1 mg/kg | −27% (n = 9) | 1.0 |

(1) "Fold change over WT" is the ratio of the "Glucose AUC reduction" of the FGF21 variant to the "Glucose AUC reduction" of FGF21-WT carried out "head to head" in the same experiment.

Mice were administered s.c. with PEGylated FGF21 wild type at 1 mg/kg, PEGylated FGF21 variants at 0.3, 1 or 3 mg/kg, or PBS vehicle at 4 ml/kg at 2 times a week for 2 weeks. On the first day of the study, tail blood glucose and body weight were measured and mice were allocated into different groups (n=8 per group) with mean glucose and body weight matched among the groups. Blood glucose was measured using a glucometer on days 1, 4, 8 and 11 before dosing and 4 hours after dosing. Additional blood glucose measurements were taken at 24 hours post each dose, on days 2, 5, 9 and 12. Plasma insulin was measured on day 1 before dosing and day 12, 24 hours post the last dose. Plasma triglycerides were measured on day 1 before dosing and day 5, 24 hours post the second dose. The results of these studies are summarized in Table 5.

TABLE 5

% changes versus vehicle in plasma glucose, insulin, triglyceride (TG), body weight (BW) gain, liver TG/lipid by PEGylated FGF21 wild type (WT) and variants during 12-day studies in ob/ob mice.

| Variant ID | Dose (mg/kg) | Total Glucose AUC | Plasma Insulin | BW gain | Liver TG (or lipid) | Plasma TG (day 5) |
|---|---|---|---|---|---|---|
| WT-N-PEG, exp 1 | 1.0 | −8% | −24% | −4% | −19% (lipid) | −48% |
| WT-N-PEG, exp 2 | 1.0 | −24% | −45% | −1% | −3% | −35% |
| WT-R154C-PEG, exp 1 | 1.0 | −30% | −40% | −5% | −18% (lipid) | −59% |
| V14-N-PEG | 0.3 | +2% | −17% | +1% | +7% | −29% |
| V14-N-PEG | 1.0 | +1% | −39% | −1% | +6% | −40% |
| V14-N-PEG | 3.0 | −11% | −39% | 0% | +7% | −24% |
| V14-L174P, R154C-PEG | 0.3 | −8% | −6% | 0% | −19% | −24% |
| V14-L174P, R154C-PEG | 1.0 | −4% | −49% | −2% | −4% | −43% |
| V14-L174P, R154C-PEG | 3.0 | −17% | −48% | −3% | −33% | −44% |
| WT-N-PEG, exp 3 | 1.0 | −8% | +21% | +1% | −5% | −17% |
| WT-R154C-PEG, exp 3 | 1.0 | −28% | −14% | −1% | −7% | −53% |
| V73-N-PEG | 0.3 | −1% | +29% | +2% | +1% | +24% |
| V73-N-PEG | 1.0 | 0% | +24% | +2% | −1% | +7% |
| V73-N-PEG | 3.0 | −16% | +8% | +3% | +8% | −22% |
| V76-154C-PEG | 0.3 | −20% | +22% | 0% | −3% | −24% |
| V76-154C-PEG | 1.0 | −20% | −21% | −1% | −25% | −45% |
| V76-154C-PEG | 3.0 | −31% | −38% | −5% | −40% | −51% |

Figure 2:
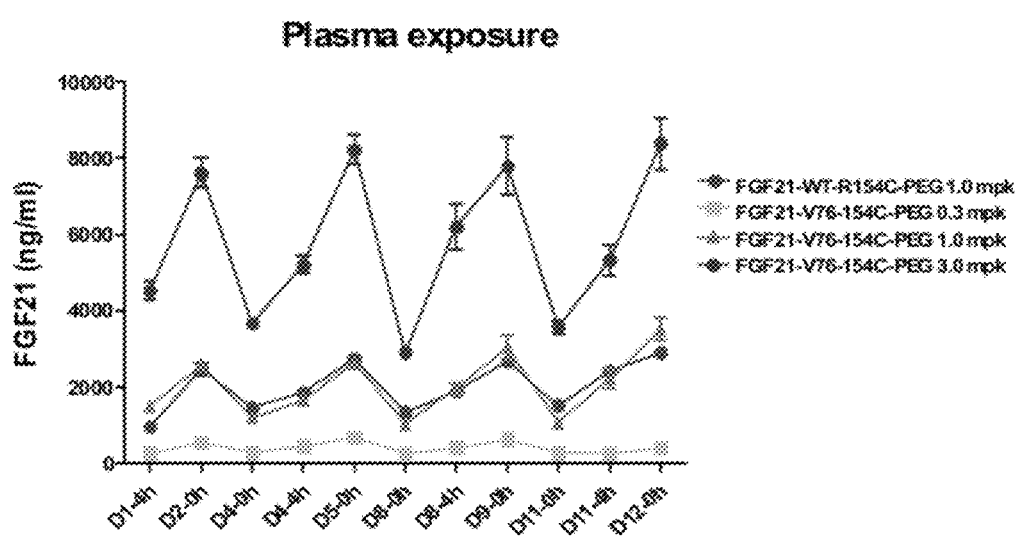
FIG. 2 is a graphical representation showing plasma exposures of FGF21-WT-R154c-PEG and FGF21-V76-154C-PEG in ob/ob mice treated for 12 days. FGF21-WT-R154C-PEG and FGF21-V76-154C-PEG were given subcutaneously on days 1, 4, 8 and 11 after 0 h time point.

The V76-154C-PEG variant exhibits an excellent in vivo metabolic profile, as seen in Table 5. V76-154C-PEG also exhibits excellent liver triglyceride lowering properties (−25% liver triglyceride change, significantly different from the vehicle control group; FIG. 1) compared with FGF21-WT-R154C-PEG (−7% Liver Triglyceride change, not significantly different from the vehicle control group; FIG. 1). When both were dosed at 1 mg/kg in the same study (WT-R154C-PEG, exp3), the plasma exposures (FIG. 2) for both compounds were equivalent and other efficacy endpoints (Total Glucose AUC, plasma insulin, body weight gain, and plasma triglycerides) were not significantly different.

Example 6

Plasma Stability Assay with Wild Type FGF21 and PEGylated FGF21 Variants

Figure 3A:
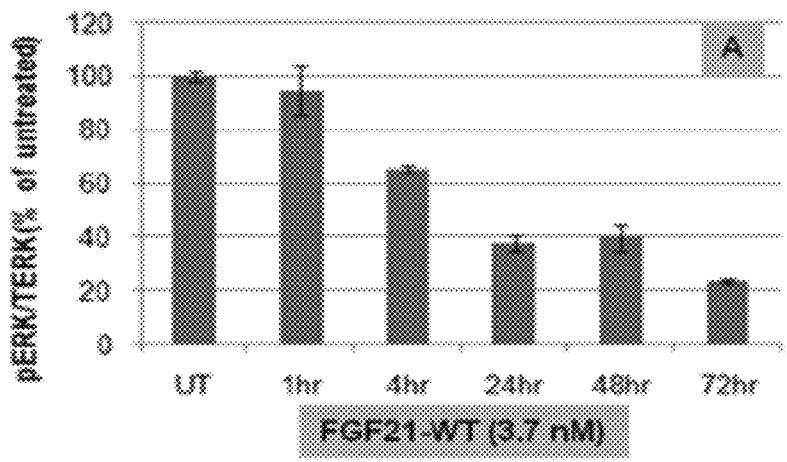
FIGS. 3A and 3B show ob/ob mouse plasma stability of wild type FGF21 (Panel A) and FGF21-V76-154C-PEG (Panel B). The average plasma contribution to the pERK activity ("background activity") is 28% (range 12-49%) for the wild type FGF21 samples and 58% (range 46-75%) for the FGF21-V76-154C-PEG samples.
Figure 3B:
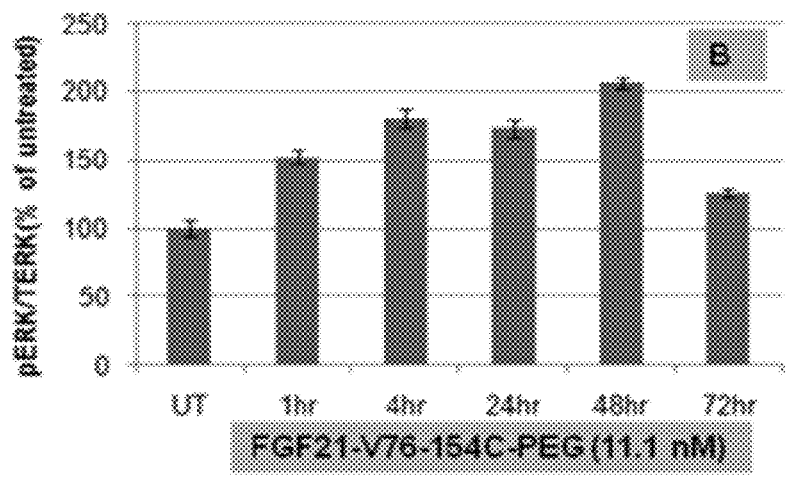

To determine the plasma stability of wild type FGF21 (FGF21-WT) in comparison to PEGylated FGF21 variants, a plasma stability assay was implemented. Ten (10) ml of FGF21-WT (4.84 mg/ml) and 35.5 µl of FGF21-V76-154C-PEG (2.12 mg/ml) were added to 90 ml and 264.5 ml of ob/ob mouse plasma (90% and 88% plasma). Each sample was made in 5 aliquots and incubated for 1 hr, 4 hr, 24 hr, 48 hr and 72 hr. Plasma-treated samples were stored at 4° C. until samples from all the time points were collected. Nine (9) µl of plasma-treated FGF21-WT and 27 µl of plasma-treated FGF21-V76-154C-PEG were added to 750 nl of medium (300 nM FGF21-WT with 1.2% plasma and 450 nM FGF21-V76-154C-PEG with 3.6% plasma) and serially diluted 1:3 in media 8 times. HEK293 cells, stably transfected with human β-klotho, were treated with proteins for 10 min followed by standard protocols of pERK ICW. Untreated FGF21-WT, FGF21-V76-154C-PEG and 1.2% and 3.6% mouse plasma are also included as controls. The results of these experiments are graphically depicted by FIGS. 3A and 3B.

While FGF21-WT lost activity over a short time frame (1-4 hours) when incubated with mouse plasma at 37° C., V76-154C-PEG by contrast retained its full activity for at least 72 hours when incubated with mouse plasma at 37° C.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention.

What is claimed is:

1. A polypeptide variant having an amino acid sequence comprising SEQ ID NO:39.

2. The variant of claim 1, wherein the variant further comprises one or more of the following modifications: (a) an amino-terminal truncation of no more than 5 amino acid residues; and (b) a carboxyl-terminal truncation of no more than 12 amino acid residues.

3. The variant of claim 1, wherein the variant is covalently linked to polyethylene glycol (PEG) or polysialic acid.

4. The variant of claim 3, wherein the polyethylene glycol (PEG) or polysialic acid comprises a branched, 40 kDa polyethylene glycol (PEG) or polysialic acid, and wherein said polyethylene glycol (PEG) or polysialic acid is covalently linked to a cysteine of the variant.

5. The variant of claim 3, wherein the PEG is attached to the cysteine residue at position 122 of SEQ ID NO:39.

6. The variant of claim 5, wherein the variant further comprises a branched, 40 kDa PEG group at position 122 of SEQ ID NO:39.

7. The variant of claim 1, wherein the variant is fused to a heterologous protein consisting of one of the following: an IgG constant domain or fragment thereof; Human Serum Albumin (HSA); and an albumin-binding polypeptides.

8. The variant of claim 7, wherein the heterologous protein is fused to the amino terminus of the variant.

9. The variant of claim 7, wherein the heterologous protein is fused to the carboxy terminus of the variant.

10. A multimer consisting of the variant of claim 1.

11. The multimer of claim 10, wherein the multimer is a homodimer.

12. A pharmaceutical composition comprising the variant of SEQ ID NO:39.

13. The pharmaceutical composition of claim 12, wherein the variant has a PEG group attached at the cysteine residue at position 122 of SEQ ID NO:39.

14. A polypeptide variant having an amino acid sequence selected from the group consisting of SEQ ID NO:16-19, 38, or 39.

15. The variant of claim 14, wherein the variant further comprises one or more of the following modifications: (a) an amino-terminal truncation of no more than 5 amino acid residues; and (b) a carboxyl-terminal truncation of no more than 12 amino acid residues.

16. The variant of claim 14, wherein the variant is covalently linked to polyethylene glycol (PEG) or polysialic acid.

17. The variant of claim 16, wherein the polyethylene glycol (PEG) or polysialic acid comprises a branched, 40 kDa polyethylene glycol (PEG) or polysialic acid, and wherein said polyethylene glycol (PEG) or polysialic acid is covalently linked to a cysteine of the variant.

18. The variant of claim 16, wherein the PEG is attached to the cysteine residue at position 122 of SEQ ID NO:39.

19. The variant of claim 18, wherein the variant further comprises a branched, 40 kDa PEG group at position 122 of SEQ ID NO:39.

20. The variant of claim 14, wherein the variant is fused to a heterologous protein consisting of one of the following: an IgG constant domain or fragment thereof; Human Serum Albumin (HSA); and an albumin-binding polypeptide.

21. The variant of claim 20, wherein the heterologous protein is fused to the amino terminus of the variant.

22. The variant of claim 20, wherein the heterologous protein is fused to the carboxy terminus of the variant.

23. A multimer consisting of at least one of the variants of claim 14.

24. The multimer of claim 23, wherein the multimer is a homodimer.

25. A pharmaceutical composition comprising a variant having a sequence selected from the group consisting of SEQ ID NO:16-19, 38, and 39.

26. The pharmaceutical composition of claim 25, wherein the variant has a PEG group attached at the cysteine residue at position 122 of SEQ ID NO:39.

27. A polypeptide variant comprising a 4 amino acid N-terminally truncated mature FGF21 wild-type protein with the following substitutions made relative to SEQ ID NO:1: a glutamic acid residue substitution at position 56, a histidine residue substitution at position 74, a lysine residue substitution at position 105, an arginine residue substitution at position 150, a glutamine residue substitution at position 159, an alanine residue substitution at position 195, and one or more amino acid substitution that is:
  (a) a glutamic acid residue substitution at position 82;
  (b) an alanine residue substitution at position 98;
  (c) an asparagine residue substitution or a glutamic acid substitution at position 130;
  (d) a cysteine residue substitution at position 154; or
  (e) a proline residue substitution at position 174.

28. The variant of claim 27, wherein the variant further comprises one or more of the following modifications: (a) an amino-terminal truncation of no more than 5 amino acid residues; and (b) a carboxyl-terminal truncation of no more than 12 amino acid residues.

29. The variant of claim 27, wherein the variant is covalently linked to polyethylene glycol (PEG) or polysialic acid.

30. The variant of claim 29, wherein the polyethylene glycol (PEG) or polysialic acid comprises a branched, 40 kDa polyethylene glycol (PEG) or polysialic acid, and wherein said polyethylene glycol (PEG) or polysialic acid is covalently linked to a cysteine of the variant.

31. The variant of claim 27, wherein the variant is fused to a heterologous protein consisting of one of the following: an IgG constant domain or fragment thereof; Human Serum Albumin (HSA); and an albumin-binding polypeptides.

32. The variant of claim 31, wherein the heterologous protein is fused to the amino terminus of the variant.

33. The variant of claim 31, wherein the heterologous protein is fused to the carboxy terminus of the variant.

34. A multimer consisting of at least one of the variants of claim 27.

35. The multimer of claim 34, wherein the multimer is a homodimer.

36. A variant of claim 27 having the cysteine residue substitution at position 122 of SEQ ID NO:39, wherein the variant is covalently linked to polyethylene glycol (PEG) or polysialic acid attached to said cysteine residue.

37. The variant of claim 36, wherein the variant further comprises a branched, 40 kDa PEG group at position 122 of SEQ ID NO:39.

38. A pharmaceutical composition comprising the variant of claim 27.

39. A pharmaceutical composition comprising the variant of claim 27 having the cysteine residue substitution at position 122 of SEQ ID NO:39, wherein the variant is covalently linked to polyethylene glycol (PEG) or polysialic acid attached to said cysteine residue.

* * * * *